US012643950B1

(12) United States Patent
Truong et al.

(10) Patent No.: US 12,643,950 B1
(45) Date of Patent: Jun. 2, 2026

(54) AUTOINJECTOR COMPRISING HIGH CONCENTRATION FORMULATION OF VEDOLIZUMAB

(71) Applicant: Takeda Pharmaceutical Company Limited, Osaka (JP)

(72) Inventors: Nobel T. Truong, Milford, MA (US); Willow Diluzio, Westford, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 653 days.

(21) Appl. No.: 16/784,052

(22) Filed: Feb. 6, 2020

Related U.S. Application Data

(60) Provisional application No. 62/802,671, filed on Feb. 7, 2019.

(51) Int. Cl.
| | |
|---|---|
| *C07K 16/28* | (2006.01) |
| *A61K 39/395* | (2006.01) |
| *A61M 5/20* | (2006.01) |
| *A61K 9/00* | (2006.01) |

(52) U.S. Cl.
CPC ........... *C07K 16/2839* (2013.01); *A61M 5/20* (2013.01); *A61K 9/0019* (2013.01); *A61K 39/39533* (2013.01); *A61M 2005/2026* (2013.01); *A61M 2005/2073* (2013.01); *A61M 2005/2086* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 6,015,662 | A | 1/2000 | Hackett, Jr. et al. |
| 6,189,195 | B1 | 2/2001 | Reilly et al. |
| 6,267,958 | B1 | 7/2001 | Andya et al. |
| 6,551,593 | B1 | 4/2003 | Ringler et al. |
| 7,147,851 | B1 | 12/2006 | Ponath et al. |
| 7,207,973 | B2 | 4/2007 | Barrelle |
| 8,021,335 | B2 | 9/2011 | Lesch, Jr. |
| 8,529,510 | B2 | 9/2013 | Giambattista et al. |
| 8,808,244 | B2 | 8/2014 | Adlon et al. |
| 8,932,591 | B2 | 1/2015 | Krause et al. |
| 8,945,564 | B2 | 2/2015 | Lu et al. |
| 9,199,038 | B2 | 12/2015 | Daniel |
| 9,248,236 | B2 | 2/2016 | Olson |
| 9,248,242 | B2 | 2/2016 | Verespej et al. |
| 9,468,723 | B2 | 10/2016 | Olson et al. |
| 9,499,620 | B2 | 11/2016 | Hsu et al. |
| 9,795,674 | B2 | 10/2017 | Parshad et al. |
| 9,867,940 | B2 | 1/2018 | Holmqvist et al. |
| 10,000,562 | B2 * | 6/2018 | Deshmukh .............. A61M 5/24 |
| 10,034,940 | B2 | 7/2018 | Liu et al. |
| 10,040,855 | B2 | 8/2018 | Diluzio et al. |
| 10,166,335 | B2 * | 1/2019 | Reber ................. A61M 5/2033 |
| 10,166,336 | B2 | 1/2019 | Lumme et al. |
| 11,560,434 | B2 | 1/2023 | Diluzio et al. |
| 2002/0147314 | A1 | 10/2002 | Briskin et al. |
| 2002/0172679 | A1 | 11/2002 | Ringler et al. |
| 2003/0235585 | A1 | 12/2003 | Fischkoff et al. |
| 2004/0009169 | A1 | 1/2004 | Taylor et al. |
| 2004/0023373 | A1 | 2/2004 | Briskin |
| 2004/0191243 | A1 | 9/2004 | Chen et al. |
| 2005/0095238 | A1 | 5/2005 | Brettman et al. |
| 2006/0159653 | A1 | 7/2006 | Saito et al. |
| 2007/0122404 | A1 | 5/2007 | O'Keefe |
| 2008/0071063 | A1 | 3/2008 | Allan et al. |
| 2009/0099641 | A1 | 4/2009 | Wu et al. |
| 2010/0098712 | A1 | 4/2010 | Adler et al. |
| 2010/0254985 | A1 | 10/2010 | Allan et al. |
| 2011/0070225 | A1 | 3/2011 | Goldbach et al. |
| 2014/0341885 | A1 * | 11/2014 | Diluzio ..................... A61P 1/18 424/133.1 |
| 2015/0045729 | A1 * | 2/2015 | Denzer ................... A61M 5/20 604/110 |
| 2016/0015600 | A1 * | 1/2016 | Weikart ............... C23C 16/045 206/524.2 |
| 2016/0213845 | A1 | 7/2016 | Holmqvist |
| 2018/0327497 | A1 | 11/2018 | Diluzio et al. |
| 2018/0346578 | A1 | 12/2018 | Diluzio et al. |

(Continued)

FOREIGN PATENT DOCUMENTS

| | | | |
|---|---|---|---|
| WO | 2009099641 | A2 | 8/2009 |
| WO | 2012151247 | A2 | 11/2012 |
| WO | 2012151248 | A2 | 11/2012 |

OTHER PUBLICATIONS

Daugherty, A. L. et al., "Formulation and Delivery issues for Monoclonal Antibody Therapeutics," Current Trends in Monoclonal Antibody Development and Manufacturing, Biotechnology: Pharmaceutical Aspects, Chapter 8, 103-129 (2010).
Wang, W., et al., "Antibody Structure, Instability, and Formulation," Journal of Pharmaceutical Sciences, vol. 96, 1-26 (2007).
Chen, et al., "Influence of histidine on the stability and physical properties of a fully human antibody in aqueous and solid forms," Pharm. Res., Dec. 2003, pp. 1952-1960, vol. 20, No. 12.
Kerwin Bae, et al., "Polysorbates 20 and 80 used in the formulation of protein biotherapeutics: structure and degradation pathways," Journal of Pharmaceutical Science, Aug. 2008, pp. 2924-2935, vol. 97, No. 8.
"Formulation and Process Development Strategies for Manufacturing Biopharmaceuticals", Feroz Jameel and Susan Hershenson (eds), John Wiley and Sons, Inc., Hoboken, USA, 2010; Front matter; p. 383-427; 469-472; 692-694.

(Continued)

*Primary Examiner* — Christine J Saoud
*Assistant Examiner* — Jon M Lockard
(74) *Attorney, Agent, or Firm* — Womble Bond Dickinson (US) LLP

(57) ABSTRACT

Anti-alpha4beta7 integrin antibody liquid formulations are described that have a high concentration of antibody, e.g., 90 mg/ml or more, have a viscosity suitable for injection for subcutaneous delivery, including by self-administration by the patient. In certain embodiments, formulations can be used in combination with an autoinjector having a suitable force of delivery given the viscosity of the formulation.

12 Claims, 3 Drawing Sheets

Specification includes a Sequence Listing.

(56) References Cited

U.S. PATENT DOCUMENTS

| | | |
|---|---|---|
| 2021/0340261 A1 | 11/2021 | Diluzio et al. |
| 2023/0312727 A1 | 10/2023 | Diluzio et al. |

OTHER PUBLICATIONS

Gokarn et al., 2008, J. Pharm. Sci., 97: 3051-3066.

Arakawa et al., Amino Acids. Nov. 2007: 33 (4): 587-605. Epub Mar. 16, 2007.

Wang W: "Instability, stabilization, and formulation of liquid protein pharmaceuticals". Int J Pharm. Aug. 20, 1999; 185 (2):129-88.

Vikas K. Sharma: Chapter 30. The Formulation and Delivery of Monoclonal Antibodies (Published Online: Nov. 17, 2009, DOI: 10.1002/9780470485408.ch30); Therapeutic Monoclonal Antibodies: From Bench to Clinic, Wiley Online Library, Editor(s): Zhiqiang An. Published Online: Nov. 17, 2009.

Qi P, et al: "Characterization of the photodegradation of a human IgG1 monoclonal antibody formulated as a high-concentration liquid dosage form", J Pharm Sci. Sep. 2009;98(9):3117-30, doi: 10.1002/jps.21617.

Murphy et al., Journal of Pharmaceutical Sciences, 101(1): 81-91, 2012.

Mueller et al., "Liquid formulations for long-term storage of monoclonal IgGs", Appl Biochem Biotechnol., (2013); 169 (4): 1431-48.

Bramham et al., "Stability of a high-concentration monoclonal antibody solution produced by liquid-liquid phase separation", MABS, (2021); vol. 13, No. 1, 7 pages.

Cleland et al., "A Specific Molar Ratio of Stabilizer to Protein is Required for Storage Stability of a Lyophilized Monoclonal Antibody," Journal of Pharmaceutical Sciences, 90:310-321 (2001).

ENTYVIO Prescribing Information (2014).

Non-Final Office Action dated Sep. 23, 2025, issued in U.S. Appl. No. 18/046,450.

* cited by examiner

100

102

106

104

110

112

114

116

SEQUENCE LISTING

```
<160> NUMBER OF SEQ ID NOS: 8

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asp Pro Ser Glu Ser Asn Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Trp Asp Tyr Ala Ile Asp Tyr Trp Gly
                100                 105                 110

Gln Gly Thr Leu Val Thr Val Ser Ser
            115                 120

<210> SEQ ID NO 2
<211> LENGTH: 5
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 2

Ser Tyr Trp Met His
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ile Asp Pro Ser Glu Ser Asn Thr Asn Tyr Asn Gln Lys Phe Lys
1               5                   10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Tyr Asp Gly Trp Asp Tyr Ala Ile Asp Tyr
1               5                   10

<210> SEQ ID NO 5
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Tyr Thr Phe Gly Gln Gly Thr Lys Val Glu Ile Lys
            100                 105                 110

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 6

Arg Ser Ser Gln Ser Leu Ala Lys Ser Tyr Gly Asn Thr Tyr Leu Ser
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ile Ser Asn Arg Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Gln Gly Thr His Gln Pro Tyr Thr
1               5
```

AUTOINJECTOR COMPRISING HIGH CONCENTRATION FORMULATION OF VEDOLIZUMAB

RELATED APPLICATIONS

This application claims the benefit of U.S. Provisional Application 62/802,671 filed on Feb. 7, 2019. The entire contents of the foregoing application is hereby incorporated by reference.

SEQUENCE LISTING

The instant application contains a Sequence Listing which has been submitted in ASCII format via EFS-Web and is hereby incorporated by reference in its entirety. Said ASCII copy, created on Feb. 5, 2020, is named T103022_1080US1_Sequence_Listing.TXT and is 4,096 bytes in size.

BACKGROUND OF THE INVENTION

Advances in biotechnology have made it possible to produce antibodies for pharmaceutical applications using recombinant DNA techniques. Because antibodies are larger and more complex than traditional organic and inorganic drugs (i.e., possessing multiple functional groups in addition to complex three-dimensional structures), the formulation of such antibodies poses special problems. For a therapeutic antibody to remain biologically active, a formulation must preserve the conformational integrity of at least a core sequence of the protein's amino acids, while at the same time protecting the protein's multiple functional groups from degradation.

Antibodies have a large number of formulation options, including the state of the formulation, e.g., lyophilized, spray-dried, liquid, and not one approach or system is suitable for all proteins. Several factors to be considered have been reported and are known in the art, including aggregation levels of the antibody in a formulation (See e.g., Wang, et al., J. Pharm Sci. 96:1-26 (2007)).

In addition to identifying a formulation in which the therapeutic antibody will remain stable, delivery of the formulation in a safe and effective way to the patient is critical. Effectively combining suitable delivery of the therapeutic antibody to the patient with a stable formulation can be challenging.

SUMMARY OF THE INVENTION

Vedolizumab is a relatively hydrophobic antibody. Coupled with the dose amounts needed for therapeutic efficacy, formulating vedolizumab is particularly challenging, especially when administered subcutaneously.

The invention relates, at least in part, to liquid pharmaceutical formulations having a high concentration of an anti-alpha4beta7 antibody, e.g., 90 mg/ml or greater, that are suitable for subcutaneous delivery to a human patient.

Liquid pharmaceutical formulations described herein provide stability as a liquid formulation which is not dependent on lyophilization, and have relatively low aggregates making them suitable for pharmaceutical use. In one embodiment, stability and safety, e.g., low level of aggregate, are coupled with a viscosity suitable for subcutaneous delivery, e.g., using an autoinjector like those described herein.

In one embodiment, the liquid pharmaceutical formulation comprises at least about 90 mg/ml of the anti-alpha4beta7 antibody; at least about 100 mg/ml of the anti-alpha4beta7 antibody; at least about 110 mg/ml of the anti-alpha4beta7 antibody; at least about 120 mg/ml of the anti-alpha4beta7 antibody; at least about 130 mg/ml of the anti-alpha4beta7 antibody; at least about 140 mg/ml of the anti-alpha4beta7 antibody; at least about 150 mg/ml of the anti-alpha4beta7 antibody; or at least about 160 mg/ml of the anti-alpha4beta7 antibody. In some aspects, the formulation comprises a concentration of the anti-alpha4beta7 antibody between about 90 mg/ml and 200 mg/ml, between about 90 mg/ml to 120 mg/ml, between about 150 mg/ml to 200 mg/ml, between about 50 mg/ml and 180 mg/ml, between about 60 mg/ml and 170 mg/ml, about 70 mg/ml and 160 mg/ml, about 100 mg/ml and 160 mg/ml, or about 108 mg/ml. In one aspect the liquid pharmaceutical formulation has an antibody concentration of about 155 mg/ml to 180 mg/ml. In some embodiments, the liquid pharmaceutical formulation contains at least about 90 mg/ml of anti-alpha4beta7 antibody; at least about 100 mg/ml of anti-alpha4beta7 antibody; at least about 105 mg/ml anti-alpha4beta7 antibody. In one embodiment, the liquid pharmaceutical formulation contains about 90 mg/ml to about 240 mg/ml of anti-alpha4beta7 antibody. In one embodiment, the liquid pharmaceutical formulation contains about 90 mg/ml to about 120 mg/ml of anti-alpha4beta7 antibody. The formulation can contain at least about 160 mg/ml anti-alpha4beta7 antibody. The formulation can contain about 150 to about 200 mg/ml antibody or about 165 mg/ml antibody.

In some aspects, the liquid pharmaceutical formulation comprises a 108 mg dose of the anti-alpha4beta7 antibody. In one embodiment, the liquid pharmaceutical formulation comprises about 54 and 300 mg, about 100 and 216 mg, about 100 and 300 mg, about 95 to 120 mg, about 200 to 230 mg, about 100 to 200 mg, or about 108 mg of the anti-alpha4beta7 antibody.

In certain embodiments, the liquid pharmaceutical formulation comprises at least 90 mg/ml of anti-alpha4beta7 antibody, a buffer, and an excipient in an amount that results in the formulation having a viscosity suitable for subcutaneous delivery via prefilled syringe, an autoinjector, or other device suitable for self-administration.

In certain embodiments, the liquid pharmaceutical formulation can also contain a surfactant, a polysorbate (e.g. polysorbate 20, polysorbate 80), a poloxamer, or any combination thereof.

The liquid pharmaceutical formulation can have a pH between about 5.5 and about 7.5. In certain embodiments, the liquid pharmaceutical formulation has a pH between about 6.0 and about 7.0. In certain embodiments, the liquid pharmaceutical formulation has a pH between about 6.2 and about 7.0. The pH of the liquid pharmaceutical formulation can be between about 6.5 and about 6.8. In certain embodiments, the liquid pharmaceutical formulation can have a pH between about 6.1 and about 7.0, or between about 6.2 and 6.8. In certain embodiments, the liquid pharmaceutical formulation has a pH of about 6.3 to 6.7.

In another aspect, the liquid pharmaceutical formulation can be used to deliver an alpha4beta7 antibody for treating an inflammatory bowel disease in a human subject. In certain embodiments, administration is subcutaneous. The administering can be self-administering. The inflammatory bowel disease can be Crohn's disease or ulcerative colitis. The inflammatory bowel disease can be moderate to severely active ulcerative colitis. The treatment can result in mucosal healing in patients suffering from moderate to severely active ulcerative colitis. The patient may have previously received treatment with at least one corticosteroid for the inflammatory bowel disease. The patient may concurrently receive treatment with at least one corticosteroid for the inflammatory bowel disease. The dosing regimen can result in a reduction, elimination or reduction and elimination of corticosteroid use by the patient.

In some embodiments, the stable liquid pharmaceutical formulation has about 1.0% or less aggregate formation after 1 month at 40 degrees Celsius. In some embodiments, the stable liquid pharmaceutical formulation has about 0.9% or less aggregate formation after 1 month at 40 degrees Celsius. In some embodiments, the stable liquid pharmaceutical formulation has about 0.8% or less aggregate formation after 1 month at 40 degrees Celsius. In some embodiments, the stable liquid pharmaceutical formulation has about 0.7% or less aggregate formation after 1 month at 40 degrees Celsius. In some embodiments, the stable liquid pharmaceutical formulation has about 0.6% or less aggregate formation after 1 month at 40 degrees Celsius. In some embodiments, the stable liquid pharmaceutical formulation has about 0.5% or less aggregate formation after 1 month at 40 degrees Celsius. In some embodiments, the stable liquid pharmaceutical formulation has about 0.4% or less aggregate formation after 1 month at 40 degrees Celsius. Aggregation can be determined according to standard SEC methods known in the art.

A liquid pharmaceutical formulation described herein has a viscosity suitable for delivery in an autoinjector, e.g., 2 to 70 cP. In one embodiment, the volume of the liquid pharmaceutical formulation in the autoinjector can be about 1 mL or less, about 0.9 mL or less, about 0.8 mL or less, about 0.6 mL or less, about 0.5 mL or less, or about 0.4 mL or less, and comprises a dose of about 100 to 110 mg of a humanized anti-alpha4beta7 antibody.

In yet another aspect, the invention relates to an article of manufacture, comprising a container, a liquid pharmaceutical formulation described herein, and instructions for its use.

In one embodiment of the invention, an autoinjector described herein is configured to deliver about 0.5 mL to about 1 mL of a formulation described herein, wherein the autoinjector comprises a tubular body portion; a syringe containing a humanized anti-alpha4beta7 antibody and including a plunger rod; a syringe holder configured to receive the syringe; and a resilient member configured to apply a force on the plunger rod to expel the medicament from the syringe when the autoinjector is activated. In one embodiment, the resilient member is a tension spring or a coil spring.

In one embodiment, the resilient member is configured to apply a force on the plunger rod between about 2-20 Newtons (N), about 3-17 N, about 4-15 N, about 7-13 N, about 5-10 N, about 5-8 N, or about 10N.

In one embodiment, the force applied by the resilient member is based, at least in part, on the viscosity of the formulation being delivered.

DETAILED DESCRIPTION OF THE INVENTION

Figure 1:
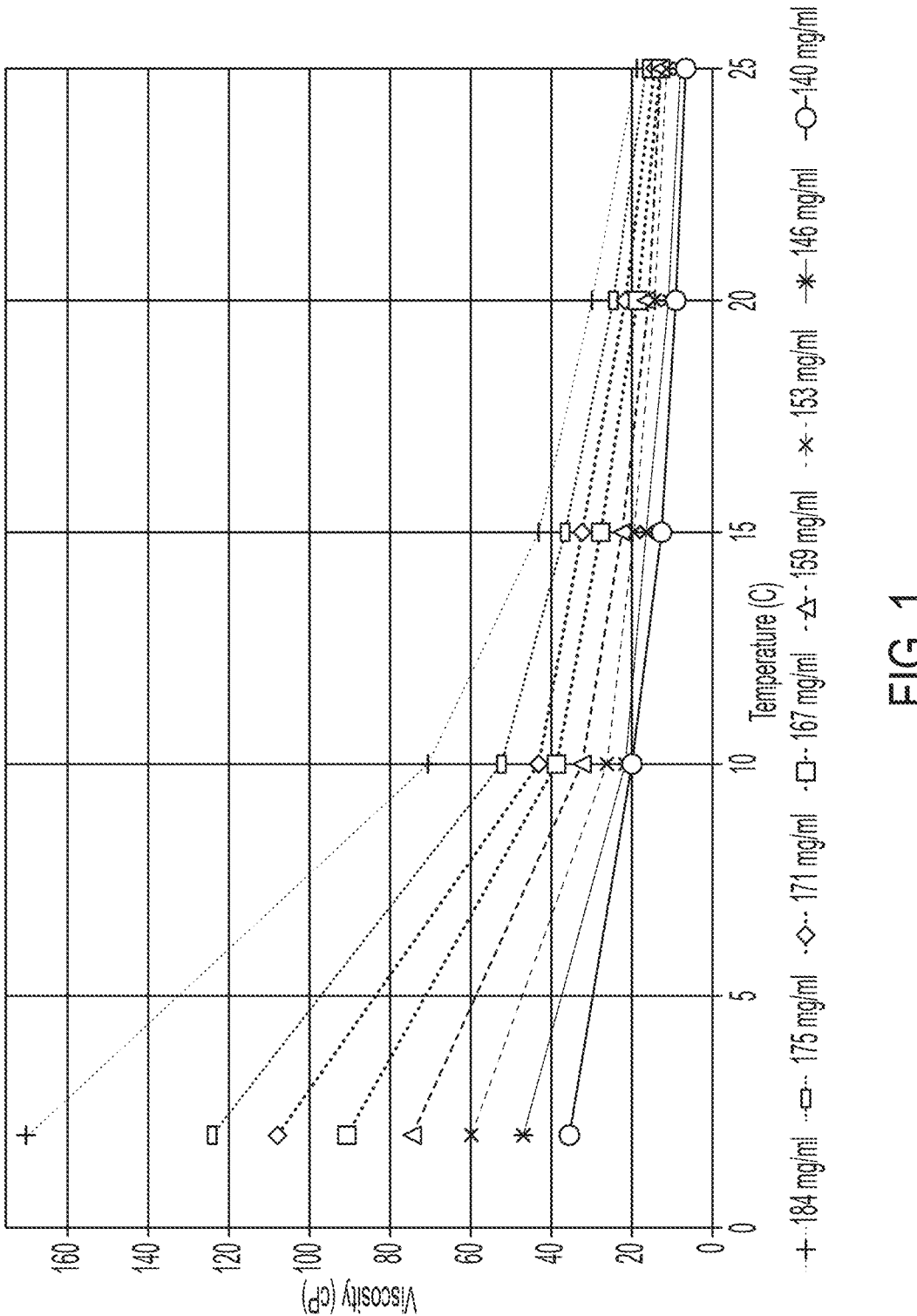
FIG. 1 graphically depicts the impact of temperature on viscosity of vedolizumab at various concentrations.

The invention relates to a pharmaceutical formulation comprising an anti-alpha4beta7 antibody suitable for delivery using a prefilled syringe.

I. Definitions

The term "pharmaceutical formulation" refers to a stable composition containing an active ingredient, such as a therapeutic antibody, in such form as to permit the biological activity of the active ingredient to be effective, and which contains no additional components which are significantly toxic to a subject to which the formulation would be administered. A pharmaceutical formulation is suitable for administration, e.g., via subcutaneous delivery, to a human subject and includes only pharmaceutically acceptable excipients, diluents, and/or other additives deemed safe by the Federal Drug Administration or other foreign national authorities. Pharmaceutical formulations include liquid, e.g., aqueous, solutions that can be directly administered.

A "stable" antibody formulation is one in which the antibody therein substantially retains its physical stability and/or its chemical stability and/or its biological activity upon storage. In one aspect, the formulation substantially retains its physical and chemical stability, as well as its biological activity upon storage. The storage period is generally selected based on the intended shelf-life of the formulation. Various analytical techniques for measuring protein stability are available in the art and are reviewed, for example, in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period. For example, a liquid formulation is stable at about 40° C. for at least about 3 days, 5 days, 1 week, 2 weeks, 3 weeks, 4 weeks, 5 weeks or 6 weeks. In one embodiment, a liquid formulation is stable at about 5° C. and/or 25° C. for at least about 1 month, at least about 3 months, at least about 6 months, at least about 9 months, at least about 12 months, at least about 18 months, at least about 24 months, at least about 30 months, or at least about 36 months; and/or stable at about −20° C. and/or −70° C. for at least about 1 month, at least about 3 months, at least about 6 months, at least about 9 months, at least about 12 months, at least about 18 months, at least about 24 months, at least about 30 months, at least about 36 months, at least about 42 months, or at least about 48 months. Furthermore, the liquid formulation may, in some embodiments, be stable following freezing (to, e.g., −80° C.) and thawing, for example following 1, 2 or 3 cycles of freezing and thawing.

The stability of a liquid formulation can be evaluated qualitatively and/or quantitatively in a variety of different ways, including evaluation of dimer, multimer and/or aggregate formation (for example using size exclusion chromatography (SEC), matrix-assisted laser desorption-ionization time-of-flight mass spectrometry (MALDI-TOF MS), analytical ultracentrifugation, light scattering (photon correlation spectroscopy, dynamic light scattering (DLS), static light scattering, multi-angle laser light scattering (MALLS)), flow-based microscopic imaging, electronic impedance (coulter) counting, light obscuration or other liquid particle counting system, by measuring turbidity, and/or by visual inspection); by assessing charge heterogeneity using cation exchange chromatography (CEX), isoelectric focusing (IEF), e.g. capillary technique (cIEF), or capillary zone electrophoresis; amino-terminal or carboxy-terminal sequence analysis; mass spectrometric analysis; SDS-PAGE or SEC analysis to compare fragmented, intact and multimeric (i.e., dimeric, trimeric, etc.) antibody; peptide map (for example tryptic or LYS-C) analysis; evaluating biological activity or antigen binding function of the antibody; and the like. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, N-terminal extension, C-terminal processing, glycosylation differences, and the like.

A "deamidated" monoclonal antibody is one in which one or more asparagine or glutamine residue thereof has been derivatized, e.g. to an aspartic acid or an iso-aspartic acid.

An antibody which is "susceptible to deamidation" is one comprising one or more residue which has been found to be prone to deamidate.

An antibody which is "susceptible to oxidation" is an antibody comprising one or more residue which has been found to be prone to oxidation.

An antibody which is "susceptible to aggregation" is one which has been found to aggregate with other antibody molecule(s), especially upon freezing, heating, drying, reconstituting and/or agitation.

An antibody which is "susceptible to fragmentation" is one which has been found to be cleaved into two or more fragments, for example at a hinge region thereof.

By "reducing deamidation" is intended to mean preventing or decreasing (e.g., to 80%, 60%, 50%, 40%, 30%, 20% or 10% of) the amount of deamidation relative to the monoclonal antibody formulated at a different pH or in a different buffer.

By "reducing oxidation" is intended to mean preventing or decreasing (e.g., to 80%, 60%, 50%, 40%, 30%, 20% or 10% of) the amount of oxidation relative to the monoclonal antibody formulated at a different pH or in a different buffer.

By "reducing aggregation" is intended to mean preventing or decreasing (e.g., to 80%, 60%, 50%, 40%, 30%, 20% or 10% of) the amount of aggregation relative to the monoclonal antibody formulated at a different pH or in a different buffer.

By "reducing fragmentation" is intended to mean preventing or decreasing (e.g., to 80%, 60%, 50%, 40%, 30%, 20% or 10% of) the amount of fragmentation relative to the monoclonal antibody formulated at a different pH or in a different buffer.

As used herein, the terms "aggregate" or "aggregates" refer to the association of two or more antibodies or antibody fragments. For example, an aggregate can be a dimer, trimer, tetramer, or a multimer greater than a tetramer, of antibodies and/or antibody fragments. Antibody aggregates can be soluble or insoluble. The association between the aggregated molecules may be either covalent or non-covalent without respect to the mechanism by which they are associated. The association may be direct between the aggregated molecules or indirect through other molecules that link them together. Examples of the latter include, but are not limited to disulfide linkages with other proteins, hydrophobic associations with lipids, charge associations with DNA, affinity associations with leached protein A, or mixed mode associations with multiple components. Aggregates can be irreversibly formed either during protein expression in cell culture, during protein purification in downstream processing, or during storage of the drug product. The presence of aggregates in a solution can be determined using, for example, size exclusion chromatography (SEC) (e.g., SEC with UV detection, SEC with light scattering detection (SEC-LSD)), field flow fractionation, analytical ultracentrifugation sedimentation velocity, or capillary electrophoresis-sodium dodecyl sulfate (CE-SDS, reduced and nonreduced).

The term "high molecular weight" or "HMW" is used to indicate an antibody complex having a molecular weight greater than a monomer antibody. In one embodiment, a HMW aggregate has a molecular weight greater than about 147 kDa. The presence of high molecular weight aggregates may be determined by standard methods known in the art, e.g., size-exclusion chromatography (SEC).

As used herein, "biological activity" of an antibody refers to the ability of the antibody to bind to antigen and result in a measurable biological response which can be measured in vitro or in vivo.

The cell surface molecule, "α4β7 integrin." "alpha4beta7", or "α4β7" (used interchangeably throughout) is a heterodimer of an α4 chain (CD49D, ITGA4) and a β7 chain (ITGB7). Human α4-integrin and β7-integrin genes GenBank (National Center for Biotechnology Information, Bethesda, Md.) RefSeq Accession numbers NM_000885 and NM_000889, respectively) are expressed by B and T lymphocytes, particularly memory CD4+ lymphocytes. Typical of many integrins, α4β7 can exist in either a resting or activated state. Ligands for α4β7 include vascular cell adhesion molecule (VCAM), fibronectin and mucosal addressin (MAdCAM (e.g., MAdCAM-1)). An antibody that binds to α4β7 integrin is referred to herein as an "anti-α4β7 antibody".

As used herein, an antibody, or antigen-binding fragment thereof, that has "binding specificity for the α4β7 complex" binds to α4β7, but not specifically to α4β1 or α4β7. Vedolizumab is an example of an antibody that has binding specificity for the α4β7 complex.

As used herein, an "isotonic" formulation has substantially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "viscosity" is a fluid's resistance to flow, and may be measured in units of centipoise (cP) or milli-Pascal-second (mPa-s), where 1 cP=1 mPa-s, at a given shear rate. Viscosity may be measured, for example, by using a viscometer. Viscosity may be measured using any other methods and in any other units known in the art (e.g. absolute, kinematic or dynamic viscosity), understanding that it is the percent reduction in viscosity afforded by use of the excipients described by the invention that is important. Regardless of the method used to determine viscosity, the percent reduction in viscosity in excipient formulations versus control formulations will remain approximately the same at a given shear rate.

As used herein, a liquid pharmaceutical formulation containing an amount of an excipient effective to "reduce viscosity" (or a "viscosity-reducing" amount or concentration of such excipient) means that the viscosity of the formulation in its final form for administration (e.g., a liquid solution) is at least 5% less than the viscosity of an appropriate control formulation, such as water, buffer, other viscosity-reducing agents such as salt, etc. and those control formulations, for example, exemplified herein. Similarly, a "reduced viscosity" formulation is a formulation that exhibits reduced viscosity compared to a control formulation.

As used herein, "buffering agent" refers to an agent that resists changes in pH by the action of its acid-base conjugate components. Examples of buffering agents include, but are not limited to, acetate, succinate, succinate, gluconate, histidine, citrate, glycylglycine, potassium phosphate, magnesium sulfate, carbonate, borate, phthalate, glutamate, and other organic acid buffers. In some embodiments, the buffering agent used in the formulations herein adjusts the pH of the formulation to about 5.0 to about 7.5, to about pH 5.5 to about 7.5, to about pH 6.0 to about 7.0, or to a pH of about 6.3 to about 6.5. In one aspect, examples of buffering agents that alone or in combination, will control the pH in the 5.0 to 7.5 range include acetate, succinate, gluconate, histidine, citrate, phosphate, maleate, cacodylate, 2-[N-morpholino]ethanesulfonic acid (MES), bis(2-hydroxyethyl)iminotris [hydroxymethyl]methane (Bis-Tris), N-[2-acetamido]-2-iminodiacetic acid (ADA), glycylglycine and other organic acid buffers. In one embodiment, a buffering agent does not include citrate. In one embodiment, a buffering agent does not include histidine.

A "histidine buffer" is a buffer comprising histidine ions. Examples of histidine buffers include histidine chloride, histidine acetate, histidine phosphate, histidine sulfate solutions. The histidine buffer or histidine-HCl buffer has a pH between about pH 5.5 to about 7.0, between about pH 6.1 to about 6.9, or about pH 6.5.

Herein, a "surfactant" refers to an agent that lowers surface tension of a liquid. In one aspect, the surfactant is a nonionic surfactant. Examples of surfactants herein include polysorbate (polyoxyethylene sorbitan monolaurate, for example, polysorbate 20 and polysorbate 80); TRITON (t-Octylphenoxypolyethoxyethanol, nonionic detergent, Union Carbide subsidiary of Dow Chemical Co., Midland Mich.); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linolcamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; sorbitan monopalmitate; and the MONAQUAT series (Mona Industries, Inc., Paterson, N.J.); polyethyl glycol (PEG), polypropylene glycol (PPG), and copolymers of poloxyethylene and poloxypropylene glycol (e.g. Pluronics/Poloxamer, PF68 etc); etc. In another aspect, the surfactant herein is polysorbate 80.

The term "chelator" refers to an agent that binds to an atom through more than one bond. In one aspect, examples of chelators herein include citrate, ethylenediaminetetraacetic acid, ethyleneglycoltetraacetic acid (EGTA), dimercaprol, diethylenetriaminepentaacetic acid, and N,N-bis(carboxymethyl)glycine. In another aspect, the chelator is not citrate.

The term "antioxidant" refers to an agent that inhibits the oxidation of other molecules. Examples of antioxidants herein include citrate, lipoic acid, uric acid, glutathione, tocopherol, carotene, lycopene, cysteine, phosphonate compounds, e.g., etidronic acid, desferoxamine and malate.

The term "antibody" as used herein, is intended to refer to an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments, the antibody has a fragment crystallizable (Fc) region. In certain embodiments, the antibody is an IgG1 isotype and has a kappa light chain.

A "CDR" or "complementarity determining region" is a region of hypervariability interspersed within regions that are more conserved, termed "framework regions" (FR). Generally CDRs impart antibody binding specificity to a target antigen.

As used herein, the term "antigen binding fragment" or "antigen binding portion" of an antibody refers to Fab, Fab', F(ab')$_2$, and Fv fragments, single chain antibodies, functional heavy chain antibodies (nanobodies), as well as any portion of an antibody having specificity toward at least one desired epitope, that competes with the intact antibody for specific binding (e.g., an isolated portion of a complementarity determining region having sufficient framework sequences so as to bind specifically to an epitope). Antigen binding fragments can be produced by recombinant techniques, or by enzymatic or chemical cleavage of an antibody.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human antibody are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable CDR loops correspond to those of a non-human antibody and all or substantially all of the FRs are those of a human antibody sequence. The humanized antibody optionally also will comprise at least a portion of an antibody constant region (Fc), typically that of a human antibody. For further details, see Jones et al., Nature 321: 522-525 (1986); Riechmann et al., Nature 332:323-329 (1988); and Presta, Curr. Op. Struct. Biol. 2:593-596 (1992).

As used herein, the term "recombinant antibody" refers to an antibody produced as the result of the transcription and translation of a gene(s) carried on a recombinant expression vector(s) that has been introduced into a host cell, e.g. a mammalian host cell. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the recombinant antibody is an IgG1.

Molar amounts and ratios of anti-alpha4beta7 antibody to other excipients described herein are calculated on the assumption of an approximate molecular weight of about 150,000 daltons for the antibody. The actual antibody molecular weight may differ from 150,000 daltons, depending on amino acid composition or post-translational modification, e.g., as dependent on the cell line used to express the antibody. Actual antibody molecular weight can be +/−5% of 150,000 daltons.

The term "monoclonal antibody" as used herein refers to an antibody obtained from a population of substantially homogeneous antibodies, i.e., the individual antibodies comprising the population are identical and/or bind the same epitope. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

An "antigen binding fragment" of an antibody is a portion of an antibody that contains at least the variable regions of the heavy and/or light chains of the antibody. Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen binding sites and is still capable of cross-linking antigen.

"Fv" is an antibody fragment which consists of a dimer of one heavy chain variable domain and one light chain variable domain in non-covalent association.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. In one aspect, the Fv polypeptide further comprises a polypeptide linker between the VH and VL domains which enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

A "full length antibody" or "intact antibody" is one which comprises an antigen binding variable region as well as a light chain constant domain (CL) and heavy chain constant domains, CH1, CH2 and CH3. The constant domains may be native sequence constant domains (e.g. human native sequence constant domains) or amino acid sequence variants thereof. In one aspect, the full length antibody has one or more effector functions.

An "amino acid sequence variant" antibody herein is an antibody with an amino acid sequence which differs from a main species antibody. Ordinarily, amino acid sequence variants will possess at least about 70%, at least about 80%, at least about 85%, at least about 90%, or at least about 95% homology with the main species antibody. The amino acid sequence variants possess substitutions, deletions, and/or additions at certain positions within or adjacent to the amino acid sequence of the main species antibody, but retain antigen binding activity. Variations in sequence of the constant regions of the antibody will have less effect on the antigen binding activity than variations in the variable regions. In the variable regions, amino acid sequence variants will be at least about 90% homologous, at least about 95% homologous, at least about 97% homologous, at least about 98% homologous, or at least about 99% homologous with the main species antibody.

"Homology" is defined as the percentage of residues in the amino acid sequence variant that are identical after aligning the sequences and introducing gaps, if necessary, to achieve the maximum percent homology. Methods and computer programs for the alignment are well known in the art.

A "therapeutic monoclonal antibody" or a "therapeutic antibody" is an antibody used for therapy of a human subject. Therapeutic monoclonal antibodies disclosed herein include anti-alpha4beta7antibodies, including vedolizumab.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and μ, respectively. The subunit structures and three-dimensional configurations of different classes of immunoglobulins are well known.

The "light chains" of antibodies from any vertebrate species can be assigned to one of two clearly distinct types, called kappa and lambda, based on the amino acid sequences of their constant domains.

"Treatment" refers to both therapeutic treatment and prophylactic or preventative measures. Those in need of treatment include those already with the disease as well as those in which the disease or its recurrence is to be prevented. Hence, the patient to be treated herein may have been diagnosed as having the disease or may be predisposed or susceptible to the disease.

The terms "patient" and "subject" are used interchangeably herein and each refer to a human.

"Clinical remission" as used herein with reference to ulcerative colitis subjects refers to a complete Mayo score of 2 or less points and no individual subscore greater than 1 point. Crohn's disease "clinical remission" refers to a CDAI score of 150 points or less.

A "clinical response" as used herein with reference to ulcerative colitis subjects refers to a reduction in complete Mayo score of 3 or greater points and 30% or greater from baseline, (or a partial Mayo score of 2 or greater points and 25% or greater from baseline, if the complete Mayo score was not performed at the visit) with an accompanying decrease in rectal bleeding subscore of 1 or greater points or absolute rectal bleeding subscore of 1 or less point. A "clinical response" as used herein with reference to Crohn's disease subjects refers to a 70 point or greater decrease in CDAI score from baseline (week 0).

"Mucosal healing" as used herein with reference to ulcerative colitis subjects refers to an endoscopic subscore of 1 point or less (e.g., Mayo subscore of 0 (normal or inactive disease) or 1 (erythema, decreased vascular pattern, mild friability)).

As used herein, "treatment failure" refers to disease worsening, a need for rescue medications or surgical intervention for treatment of ulcerative colitis or Crohn's disease.

A rescue medication is any new medication or any increase in dose of a baseline medication required to treat new or unresolved ulcerative colitis or Crohn's disease symptoms (other than antidiarrheals for control of chronic diarrhea).

II. Formulations

A challenge of subcutaneously delivering an anti-alpha4beta7 antibody (e.g., vedolizumab) liquid pharmaceutical formulation, is that such formulations may have high viscosity related, at least in part, to a high antibody concentration and the need for providing an effective dose of the antibody. Liquid pharmaceutical formulations having high viscosity frequently makes the liquid formulation difficult for manufacturing and injecting into a human patient. One solution to a liquid pharmaceutical formulation having a high viscosity, which can be unpleasant for the patient, is the use of lower gauge needles, e.g., less than or equal to 24 gauge.

Described herein are liquid pharmaceutical formulations containing a therapeutic anti-alpha4beta7 antibody, e.g., vedolizumab, that have a high concentration of antibody, e.g., 90 mg/ml or greater, an effective dose of the antibody, and have a viscosity that is suitable for subcutaneous delivery using a needle having a gauge greater than 24, despite the antibody concentration. Liquid pharmaceutical formulations described herein are suitable for subcutaneous delivery using a suitable device, e.g., pre-filled syringe or autoinjector.

A liquid pharmaceutical formulation described herein has a viscosity measurement suitable for subcutaneous delivery to a human patient, wherein the viscosity is, for example, less than about 40 cP at about 25 degrees Celsius; less than about 38 cP at about 25 degrees Celsius; less than about 36 cP at about 25 degrees Celsius; less than about 34 cP at about 25 degrees Celsius; less than about 32 cP at about 25 degrees Celsius; less than about 30 cP at about 25 degrees Celsius; less than about 28 cP at about 25 degrees Celsius; less than about 26 cP at about 25 degrees Celsius; less than about 24 cP at about 25 degrees Celsius; less than about 22 cP at about 25 degrees Celsius; less than about 20 cP at about 25 degrees Celsius. In one embodiment, the viscosity of a liquid pharmaceutical formulation described herein is about 5 cP to about 30 cP at about 25 degrees Celsius; about 10 cP to about 30 cP at about 25 degrees Celsius; about 10 cP to about 25 cP at about 25 degrees Celsius. Such viscosities are achieved in liquid pharmaceutical antibody formulations despite having an anti-alpha4beta7 antibody concentration of about 90 mg/ml to about 280 mg/ml; of about 100 mg/ml to about 200 mg/ml; of about 90 mg/ml to about 120 mg/ml; of about 150 mg/ml to about 200 mg/ml; of about 90 mg/ml to about 260 mg/ml; of about 90 mg/ml to about 240 mg/ml; of about 90 mg/ml to about 220 mg/ml; of about 90 mg/ml to about 200 mg/ml; of about 90 mg/ml to about 180 mg/ml; of about 100 mg/ml to about 280 mg/ml; of about 100 mg/ml to about 260 mg/ml; about 100 mg/ml to about 240 mg/ml; about 100 mg/ml to about 220 mg/ml; about 100 mg/ml to about 200 mg/ml.

Despite the high antibody concentration, the liquid pharmaceutical formulations described herein maintain a viscosity level suitable for subcutaneous delivery and remain stable, e.g., have antibody aggregation levels of about 1% or less, as determined by SEC.

Formulation parameters that can affect liquid pharmaceutical formulation stability include protein concentration, pH, buffer type, buffer concentration, ionic strength, stabilizer type, and stabilizer concentration. Examples of excipients for antibody formulations include, for example, ionic salts, polysaccharides, amino acids, antioxidants, chelators, and surfactants.

In some embodiments, liquid pharmaceutical formulations herein may contain an amount of an excipient effective to reduce viscosity (or a viscosity-reducing amount or concentration of such excipient). Excipients include, for example, polyols such as sorbitol or mannitol; sugars such as sucrose, lactose or dextrose; polymers such as polyethylene glycol; salts such as NaCl, KCl or calcium phosphate; propylene glycol; amino acids, including, for example, proline, glycine or methionine; surfactants; metal ions; and/or buffer salts such as glutamate, acetate or aspartate. Excipients can comprise sugars, for example sugar alcohols, reducing sugars, non-reducing sugars and sugar acids.

Further examples of excipients include but are not limited to sugars/polyols such as: sucrose, lactose, glycerol, xylitol, sorbitol, mannitol, maltose, inositol, trehalose, glucose.

In one embodiment, liquid pharmaceutical formulations described herein contain surfactants such as a polysorbate, e.g., Tween-80™ (polysorbate 80) or Tween-20™ (polysorbate 20).

In one embodiment, liquid pharmaceutical formulations described herein potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate or any combination of the above.

In one embodiment, aggregate formation can be reduced by removing oxygen from the formulation. Alternatively, the liquid pharmaceutical formulation can contain an antioxidant or chelator. In one aspect, exemplary antioxidants and chelators that can be included in the formulation include lipoic acid, uric acid, glutathione, tocopherol, carotene, lycopene, cysteine, ethylenediaminetetraacetic acid (EDTA), ethyleneglycoltetraacetic acid (EGTA), dimercaprol, diethylenetriaminepentaacetic acid, and N,N-bis(carboxymethyl)glycine, phosphonate compounds, e.g., etidronic acid, desferoxamine, malate and citrate. Some antioxidants and chelators can decrease the rate of aggregate formation during storage of the formulation. In another aspect, the chelator and/or antioxidant is citrate or EDTA. Exemplary chelator concentrations for liquid pharmaceutical formulations are in the range of from about greater than 0 mM to about 60 mM, about 5 mM to about 50 mM, about 5 mM to about 15 mM, about 10 mM to about 25 mM, and about 20 to about 30 mM. In another aspect, the chelator concentration is from about 0 mM to about 30 mM. In one embodiment, the chelator and/or antioxidant is citrate, and the citrate concentration is from about 0 mM to about 15 mM, about 0 mM to about 10 mM, about 2 to 7 mM, about 2 to 12 mM, or about 0 mM to about 5 mM.

The liquid pharmaceutical formulation can contain any desired one free amino acid, which can be in the L-form, the D-form or any desired mixture of these forms. In one aspect, free amino acids that can be included in the formulation include, for example, asparagine, glutamine, histidine, alanine, arginine, glycine, glutamic acid, serine, lysine, tryptophan, valine, cysteine and combinations thereof. Some amino acids can stabilize the proteins against degradation during manufacturing, drying, lyophilization and/or storage, e.g., through hydrogen bonds, salt bridges, antioxidant properties, or hydrophobic interactions or by exclusion from the protein surface. Amino acids can act as tonicity modifiers or can act to decrease viscosity of the formulation. In another aspect, free amino acids, such as histidine and arginine, can act as lyoprotectants, and do not crystallize when lyophilized as components of the formulation. Free amino acids, such as glutamic acid and histidine, alone or in combination, can act as buffering agents in aqueous solution in the pH range of 5 to 7.5. In still yet another aspect, the formulation contains histidine, arginine, or a combination of histidine and arginine. In still yet another aspect, free amino acid concentrations for liquid formulations are in the range from about 9 mM to about 0.5 M, for example, from about 10 mM to about 90 mM, about 10 mM to about 75 mM, about 10 mM to about 40 mM, about 25 mM to about 50 mM, about 15 mM to about 300 mM, about 20 mM to about 200 mM, about 25 mM to about 150 mM, about 50 mM to about 75 mM, about 50 mM to about 120 mM, about 50 to about 150 mM, or about 50 mM or about 125 mM.

The liquid pharmaceutical formulation can optionally further contain at least one surfactant, e.g., to control soluble and insoluble aggregate formation. In one aspect, the surfactant is a non-ionic surfactant. In another aspect, the surfactant is an ionic surfactant. Exemplary surfactants that can be included in the formulation include, for example, polysorbate 20, polysorbate 80, a poloxamer (Pluronic®) and combinations thereof. Surfactants can be ionic or non-ionic. Exemplary non-ionic surfactants that can be included in the liquid pharmaceutical formulations herein include, e.g., alkyl poly(ethylene oxide), alkyl polyglucosides (e.g., octyl glucoside and decyl maltoside), fatty alcohols such as cetyl alcohol and oleyl alcohol, cocamide MEA, cocamide DEA, and cocamide TEA. Specific non-ionic surfactants that can be included in liquid pharmaceutical formulations described herein include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 188, poloxamer 407; polyethylene-polypropylene glycol; or polyethylene glycol (PEG). Polysorbate 20 is also known as TWEEN 20, sorbitan monolaurate and polyoxyethylenesorbitan monolaurate. Ionic surfactants can include, for example, anionic, cationic and zwitterionic surfactants. Anionic surfactants include, for example, sulfonate-based or carboxylate-based surfactants such as soaps, fatty acid salts, sodium dodecyl sulfate (SDS), ammonium lauryl sulfate and other alkyl sulfate salts. Cationic surfactants include, for example, quaternary ammonium-based surfactants such as cetyl trimethyl ammonium bromide (CTAB), other alkyltrimethyl ammonium salts, cetyl pyridinium chloride, polyethoxylated tallow amine (POEA) and benzalkonium chloride. Zwitterionic or amphoteric surfactants include, for example, dodecyl betaine, dodecyl dimethylamine oxide, cocamidopropyl betaine and coco ampho glycinate.

When present, the surfactant is generally included in an amount which reduces formation of insoluble aggregates of antibody, e.g., during bottling, freezing, drying, lyophilization and/or reconstitution, in the presence of silicone, filling vials, prefilled syringes, and/or cartridges. In some embodiments, the formulations may contain about 0.01% to about 10% surfactant; about 0.05% to about 5% surfactant; or about 0.1% to about 1% surfactant. For example, the formulations herein may comprise about 0.01%; about 0.02%; about 0.03%; about 0.04%; about 0.05%; about 0.06%; about 0.07%; about 0.08%; about 0.09%; about 0.10%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; or about 0.30% surfactant. The surfactant concentration is generally from about 0.0001% to about 1.0%, from about 0.01% to about 0.5%, for example, about 0.05%, 0.1%, 0.15%, 0.20%, 0.3%, 0.4%, or 0.5% (w/v). Higher concentrations of surfactant, e.g., polysorbate 80 can lead to more SEC aggregate formation. Reducing the concentration of polysorbate 80 can reduce SEC aggregate formation upon storage. In one aspect, the surfactant:antibody molar ratio is from about 0.7:1 to about 2.0:1. In another aspect, the surfactant: antibody molar ratio is 1.5:1.

The liquid pharmaceutical formulations herein may also comprise one or more carbohydrates, e.g., one or more sugars. The sugar can be a reducing sugar or a non-reducing sugar. Reducing sugars include, e.g., sugars with a ketone or aldehyde group and contain a reactive hemiacetal group, which allows the sugar to act as a reducing agent. Specific examples of reducing sugars include fructose, glucose, glyceraldehyde, lactose, arabinose, mannose, xylose, ribose, rhamnose, galactose and maltose. Non-reducing sugars can comprise an anomeric carbon that is an acetal and is not substantially reactive with amino acids or polypeptides to initiate a Maillard reaction. Specific examples of non-reducing sugars include sucrose, trehalose, sorbose, sucralose, sorbitol, melezitose and raffinose. Sugar acids include, for example, saccharic acids, gluconate and other polyhydroxy sugars and salts thereof.

The amount of sugar contained within a liquid pharmaceutical formulation herein will vary in order to achieve viscosity levels suitable for subcutaneous delivery. In certain embodiments, a liquid pharmaceutical formulation may contain about 0.1% to about 20% sugar; about 0.5% to about 20% sugar; about 1% to about 20% sugar; about 2% to about 15% sugar; about 3% to about 10% sugar; about 4% to about 10% sugar; or about 5% to about 10% sugar. For example, the pharmaceutical formulations of the present invention may comprise about 0.5%; about 1.0%; about 1.5%; about 2.0%; about 2.5%; about 3.0%; about 3.5%; about 4.0%; about 4.5%; about 5.0%; about 5.5%; about 6.0%; 6.5%; about 7.0%; about 7.5%; about 8.0%; about 8.5%; about 9.0%; about 9.5%; about 10.0%; about 10.5%; about 11.0%; about 11.5%; about 12.0%; about 12.5%; about 13.0%; about 13.5%; about 14.0%; about 14.5%; about 15.0%; about 15.5%; about 16.0%; 16.5%; about 17.0%; about 17.5%; about 18.0%; about 18.5%; about 19.0%; about 19.5%; or about 20.0% sugar (e.g., sucrose).

In one embodiment, a liquid pharmaceutical formulation comprising an anti-alpha4beta7 antibody comprises a buffering agent. Examples of buffering agents that may be used in the formulations described herein include, but are not limited to, acetate, succinate, succinate, gluconate, histidine, citrate, glycylglycine, and other organic acid buffers. In some embodiments, a buffering agent used in liquid pharmaceutical formulations herein is a buffering agent that is suitable to adjust the pH of the formulation to about 5.0 to about 7.5, to about pH 5.5 to about 7.5, to about pH 6.0 to about 7.0, or to a pH of about 6.3 to about 6.5. In one aspect, examples of buffering agents that alone or in combination, will control the pH in the 5.0 to 7.5 range include acetate, succinate, gluconate, histidine, citrate, phosphate, maleate, or cacodylate. In one embodiment, a buffering agent does not include citrate. In one embodiment, a buffering agent does not include histidine.

An embodiment of a liquid pharmaceutical anti-alpha4beta7 antibody formulation described herein is that the formulation contains a high concentration of anti-alpha4beta7 antibody. For example, in one embodiment, the liquid pharmaceutical formulations can comprise at least about 90 mg/ml, at least about 100 mg/ml, at least about 110 mg/ml, at least about 120 mg/ml, at least about 130 mg/ml, at least about 140 mg/ml, at least about 150 mg/ml, at least about 160 mg/ml, at least about 170 mg/ml, at least about 180 mg/ml, at least about 190 mg/ml, at least about 200 mg/ml, at least about 250 mg/ml, at least about 300 mg/ml, from about 90 mg/ml to about 190 mg/ml, from about 90 mg/ml to about 170 mg/ml anti-alpha4beta7 antibody, from about 85 to 120 mg/ml, from about 90 mg/ml to 110 mg/ml, from about 150 mg/ml to about 180 mg/ml, or about 160 mg/ml or about 165 mg/ml anti-alpha4beta7 antibody.

In one embodiment, a liquid pharmaceutical formulation described herein provides a 100 to 110 mg dose of the antibody in a volume of 0.4 ml to 1.1 ml; a 100 to 110 mg dose of the antibody in a volume of 0.45 ml to 1.05 ml; a 100 to 110 mg dose of the antibody in a volume of 0.5 ml to 1.0 ml; a 100 to 110 mg dose of the antibody in a volume of 0.55 ml to 1 ml; a 100 to 110 mg dose of the antibody in a volume of 0.6 ml to 1 ml; a 100 to 110 mg dose of the antibody in a volume of 0.65 ml to 1 ml; a 100 to 110 mg dose of the antibody in a volume of 0.7 ml to 1 ml. In one embodiment, the dose of the antibody provided in the liquid pharmaceutical formulation which is contained in a subcutaneous delivery device, like those described herein, is about 108 mg. In one embodiment, the dose of the antibody provided in the liquid pharmaceutical formulation which is contained in a subcutaneous delivery device, like those described herein, is about 100 to 110 mg in a volume of about 0.6 to 1.0 ml; about 0.6 to about 0.9 ml; about 0.6 to 0.8 ml; or about 0.6 to 0.7 ml.

Liquid pharmaceutical formulations disclosed herein have a pH between about 5.5 and about 7.5, between about 6.0 and 7.3, between about 6.0 and about 7.0, between about 6.0 and 6.5, between about 6.0 and 6.3, between about 6.3 and 7.1, or between about 6.4 and 7.0, or between 6.3 and 6.8, such as about 6.0, 6.1, 6.2, 6.3, 6.4, 6.5, 6.6, 6.7, 6.8, or 6.9. Liquid formulations can be kept at room temperature, refrigerated (e.g., 2-8° C.), or frozen (e.g., −20° C. or −70° C.) for storage. It should be noted that a liquid pharmaceutical formulation as described herein does not include a reconstituted lyophilized formulation.

The liquid pharmaceutical formulation should be sterile, and this can be achieved according to the procedures known to the skilled person for generating sterile pharmaceutical formulations suitable for administration to human subjects, prior to, or following, preparation of the formulation. The formulation can be sterilized as a liquid, e.g., by filtration through small pores, through aseptic processing or by exposure to ultraviolet radiation. Filter pore sizes can be 0.1 μm or 0.2 μm to filter microorganisms or 10 to 20 nm to filter virus particles.

In one aspect, the liquid pharmaceutical formulation is stable upon storage. Various stability assays are available to the skilled practitioner for confirming the stability of the liquid pharmaceutical formulation. For example, the antibody in the liquid pharmaceutical formulation may be stable upon storage at about 25° C. for at least about 4 weeks, at least about 2 months, at least about 3 months, or at least about 6 months, or at least about 9 months, or at least about 12 months; at about 2-8° C. at least about 3 months, at least about 1 year, at least about 2 years, at least about 3 years or longer. Alternatively or in addition, the antibody in the liquid pharmaceutical formulation may be stable upon storage at about 15° C. for at least about 4 weeks, at least about 3 months, at least about 6 months, at least about 9 months, at least about 1 year, or longer. Alternatively or in addition, the antibody in the formulation may be stable upon storage at about −20° C. or −70° C. for at least about 4 weeks; at least about 3 months, at least about 6 months, at least about 9 months, at least about 1 year, at least about 2 years, at least about 3 years, at least about 4 years or longer.

In some embodiments, the stable liquid pharmaceutical formulation has about 1.0% or less aggregate formation after 1 month at 40 degrees Celsius. In some embodiments, the stable liquid pharmaceutical formulation has about 0.9% or less aggregate formation after 1 month at 40 degrees Celsius. In some embodiments, the stable liquid pharmaceutical formulation has about 0.8% or less aggregate formation after 1 month at 40 degrees Celsius. In some embodiments, the stable liquid pharmaceutical formulation has about 0.7% or less aggregate formation after 1 month at 40 degrees Celsius. In some embodiments, the stable liquid pharmaceutical formulation has about 0.6% or less aggregate formation after 1 month at 40 degrees Celsius. In some embodiments, the stable liquid pharmaceutical formulation has about 0.5% or less aggregate formation after 1 month at 40 degrees Celsius. In some embodiments, the stable liquid pharmaceutical formulation has about 0.4% or less aggregate formation after 1 month at 40 degrees Celsius.

Stability can be tested by evaluating physical stability, chemical stability, and/or biological activity of the antibody in the formulation around the time of formulation as well as following storage at the noted temperatures. Physical and/or chemical stability of a liquid formulation or a reconstituted dry powder can be evaluated qualitatively and/or quantitatively in a variety of different ways (see, e.g., Analytical Techniques for Biopharmaceutical Development, Rodriguez-Diaz et al. eds. Informa Healthcare (2005)), including evaluation of soluble and insoluble aggregate formation (for example using size exclusion chromatography, analytical ultracentrifugation, MALDI-TOF MS, light scattering (dynamic (DLS) or MALLS), flow-based microscopic imaging, or other liquid particle counting system, by measuring turbidity, by density gradient centrifugation and/or by visual inspection); by assessing charge heterogeneity using cation exchange chromatography (see also Vlasak and Ionescu, Curr. Pharm. Biotechnol. 9:468-481 (2008) and Harris et al. J. Chromatogr. B Biomed. Sci. Appl. 752:233-245 (2001)), isoelectric focusing or capillary zone electrophoresis; amino-terminal or carboxy terminal sequence analysis; mass spectrometric analysis; SDS-PAGE analysis to compare fragmented, intact and multimeric (i.e., dimeric, trimeric, etc.) antibody; peptide map (for example tryptic or LYS- and the like). Instability may result in aggregation, deamidation (e.g., Asn deamidation), oxidation (e.g., Met oxidation), isomerization (e.g., Asp isomerization), denaturation, clipping/hydrolysis/fragmentation (e.g., hinge region fragmentation), succinimide formation, unpaired cysteine(s), N-terminal extension, C-terminal processing, glycosylation differences, etc. Biological activity or antigen binding function, e.g., binding of the anti-alpha4beta7 antibody to MAdCAM (e.g., MAdCAM-1) or inhibition of the binding of a cell expressing alpha4beta7integrin to MAdCAM (e.g., MAdCAM-1), e.g., immobilized MAdCAM (e.g., MAdCAM-1), can be evaluated using various techniques available to the skilled practitioner (see e.g., Soler et al., J. Pharmacol. Exper. Ther. 330:864-875 (2009)).

A stable liquid pharmaceutical formulation can contribute to a low immunogenicity of an anti-alpha4beta7 antibody. An immunogenic anti-alpha4beta7 antibody can lead to a human-anti-human antibody (HAHA) response in human subjects or patients. Patients who develop a HAHA response to an anti-alpha4beta7 antibody can have adverse events (e.g., site infusion reaction) upon treatment or can eliminate anti-alpha4beta7 antibody quickly, resulting in a lower dose than planned by treatment. A report (Feagen et al. (2005) N. Engl. J. Med. 352:2499-2507) of early study of an anti-alpha4beta7 antibody treatment indicated that human anti-human antibodies developed by week 8 in 44% of treated patients. The antibody in this study was stored as a liquid and did not contain any polysorbate.

In some embodiments, the liquid pharmaceutical formulation can increase the proportion of HAHA negative patients to at least 40%, at least 50%, at least 60%, at least 70%, at least 80% or at least 90% of patients compared to the HAHA results of a less stable formulation.

In some embodiments, an anti-alpha4beta7 antibody liquid pharmaceutical formulation has <50% major charged isoform, <55% major charged isoform, or 65 to 70% major charged isoform. In other aspects, a stable anti-alpha4beta7 antibody liquid pharmaceutical formulation has less than or equal to 45% acidic charged isoforms, less than or equal to 40% acidic charged isoforms, less than or equal to 30% acidic charged isoforms or 22 to 28% acidic isoforms. In still other aspects, a stable anti-alpha4beta7 antibody liquid pharmaceutical formulation has less than or equal to 25% basic isoforms, less than or equal to 20% basic isoforms, less than or equal to 15% basic isoforms, about 5% basic isoforms or about 10% basic isoforms. In one aspect, a stable anti-alpha4beta7 antibody liquid pharmaceutical formulation has greater than or equal to 55% major isoform, less than or equal to 30% acidic isoforms and/or less than or equal to 20% basic isoforms, e.g., as determined by CEX. In another aspect, a stable anti-alpha4beta7 antibody liquid pharmaceutical formulation has greater than or equal to 50% major isoform, less than or equal to 45% acidic isoforms and/or <10% basic isoforms, e.g., as determined by cIEF.

Monomeric content and/or aggregate content (e.g., as dimers, trimers, tetramers, pentamers, oligomers and higher-order aggregates), i.e., in the liquid formulation, or in the reconstituted formulation, can be measured by SEC, analytical ultracentrifugation, light scattering (DLS or MALLS), MALDI-TOF MS or nanoscale measurement, such as nanoparticle tracking analysis NTA, NanoSight Ltd, Wiltshire, UK). Resolution, characterization and quantification of aggregate can be achieved in a number of ways, including increasing the length of the SEC column separation, e.g., by a longer column or by serial attachment of a second or more SEC column(s) in line with the initial analytical SEC column, supplementing SEC quantification of monomers with light scattering, or by using NTA.

In one embodiment, an anti-alpha4beta7 antibody liquid pharmaceutical formulation has greater than or equal to 90% monomeric antibody, greater than or equal to 95% monomeric antibody, or 97 to 99% monomeric antibody. In another embodiment, the majority of the material in an anti-alpha4beta7 antibody liquid pharmaceutical formulation has an average radius of less than or equal to 20 nm, less than or equal to 15 nm, less than or equal to 10 nm, or about 5 to about 7 nm. In one aspect, an anti-alpha4beta7 antibody liquid pharmaceutical formulation has 80% amount heavy plus light chain by protein analysis. In one aspect, there is 90% heavy plus light chain. In another aspect, an anti-alpha4beta7 antibody liquid pharmaceutical formulation has less than or equal to 10% aggregate, less than or equal to 5% aggregate, less than or equal to 2.5% aggregate, less than or equal to 1.5% aggregate, less than or equal to 1.0% aggregate or less than or equal to 0.5% aggregate. In another aspect, stable anti-alpha4beta7 antibody liquid pharmaceutical formulation has greater than or equal to 96% monomer and/or less than or equal to 2.5% aggregate. In yet another aspect, a stable anti-alpha4beta7 antibody liquid pharmaceutical formulation has about 99% monomer and/or about ≤1% aggregate.

Particle sizes, greater than 1 to 2 micron, e.g., of aggregates or undissolved excipient, i.e., in the liquid pharmaceutical formulation can be measured by light obscuration (e.g., liquid particle counting system (HIAC) by Hach Ultra Analytics (Grants Pass, Oreg.)), microscopy, coulter counter, or digital (e.g., flow-based) microscopic imaging based system such as microfluidics imaging (MFI) by Brightwell (Ottawa, Calif.) or FLOWCAM® Image particle analyzer by Fluid Imaging Technologies (Yarmouth, Me.). In one aspect, particle size in an anti-alpha4beta7 antibody liquid pharmaceutical formulation is about 30 μm, about 25 μm, about 10 μm, about 5 μm, about 2 μm or 1 μm or less. The amount of particles should be minimized in antibody liquid pharmaceutical formulations. In one aspect, an amount of particles in an anti-alpha4beta7 antibody liquid pharmaceutical formulation is <6000 particles greater than or equal to 10 μm diameter and/or <600 particles greater than or equal to 25 μm diameter in one dose (U.S. Pharmacopoeia Chp. 788, light obscuration counting method; half those amounts by microscopic quantification method). In another aspect, an amount of particles in a dose of an anti-alpha4beta7 antibody liquid pharmaceutical formulation is about 1000 particles greater than or equal to 10 μm and about 0-100 particles greater than or equal to 25 μm (MFI method). In yet another aspect, an amount of particles per milliliter, e.g., by MFI measurement, in a dose of an anti-alpha4beta7 antibody formulation is about 500 to about 2000 of 2-10 μm particles per ml, about 50 to about 350 of greater than or equal to 10 μm particles per ml and about 0 to about 50 of greater than or equal to 25 μm particles per ml. In yet another aspect, an amount of particles in a dose of an anti-alpha4beta7 antibody liquid pharmaceutical formulation is about 500 to about 100,000, about 1000 to about 5000 or about 1500 to about 3000 of 2-10 μm particles per ml.

An advantage of the liquid pharmaceutical formulations provided herein is that they have suitable levels of viscosity for delivering a dose of an anti-alpha4beta7 antibody subcutaneously in a human patient. The viscosity of an anti-alpha4beta7 antibody liquid pharmaceutical formulation can be controlled for subcutaneous or intramuscular administration. The viscosity can be affected by protein concentration and pH. For example, as the protein concentration increases, the viscosity can increase. An increase in pH can decrease the viscosity of the anti-alpha4beta7 antibody liquid pharmaceutical formulation. In some liquid pharmaceutical formulations, sodium chloride is added to reduce the viscosity of the liquid pharmaceutical formulation. Additional components that can affect viscosity of an anti-alpha4beta7 antibody formulation are amino acids.

An anti-alpha4beta7 antibody liquid pharmaceutical formulation can be isotonic (e.g., 250-350 mOsm) or hypertonic (e.g., greater than 350 mOsm, greater than 450 mOsm, greater than 550 mOsm or greater than 650 mOsm), e.g., for subcutaneous or intramuscular administration. In one aspect, the anti-alpha4beta7 antibody liquid pharmaceutical formulation is not hypotonic, e.g., less than 250 mOsm. In another aspect, the anti-alpha4beta7 antibody liquid pharmaceutical formulation is about 350 to about 400 mOsm, about 400 to about 450 mOsm or about 350 to about 450 mOsm.

Instability leading to denaturation can be assessed by differential scanning calorimetry (DSC). Antibodies have two melting temperatures (Tm) in DSC, e.g., Tm1 and Tm2. Certain excipients can affect the stability of the native anti-alpha4beta7 antibody. A finding of a higher melting temperature when comparing liquid pharmaceutical formulations by DSC can indicate a more stable anti-alpha4beta7 antibody liquid pharmaceutical formulation with the higher Tm. For example, at pH5.7, the Tm of an anti-alpha4beta7 antibody liquid pharmaceutical formulation is lower, and thus less stable than at pH 6.5. In one aspect, Tm1 of an anti-alpha4beta7 antibody liquid pharmaceutical formulation is >60° C. In another aspect, the Tm1 of an anti-alpha4beta7 antibody liquid pharmaceutical formulation is about 65° C. to about 70° C. or about 69° C. In one aspect, Tm2 of an anti-alpha4beta7 antibody liquid pharmaceutical formulation is >80° C. In another aspect, the Tm2 of an anti-alpha4beta7 antibody liquid pharmaceutical formulation is about 82° C. to about 88° C. or about 86° C.

In one embodiment, an anti-alpha4beta7 antibody liquid pharmaceutical formulation has a binding affinity or EC50 value of about 60% to about 140% of the reference standard anti-alpha4beta7 antibody. In one aspect, an anti-alpha4beta7 antibody in a liquid pharmaceutical formulation described herein binds to alpha 4beta 7, e.g., on a cell (WO98/06248 or U.S. Pat. No. 7,147,851), at a value of about 80% to about 120% of the reference standard. In another embodiment, an anti-alpha4beta7 antibody formulation has the ability to inhibit at least 50%, or at least 60% of the binding of a cell expressing alpha4beta7integrin to MAdCAM (e.g., MAdCAM-1), e.g., a MAdCAM-Ig chimera (see U.S. Patent Application Publication No. 20070122404, also for reference standard examples).

As noted above, freezing of the liquid pharmaceutical formulation is specifically contemplated herein. Hence, the liquid pharmaceutical formulation can be tested for stability upon freezing and thawing. Accordingly, the antibody in a liquid formulation may be stable upon freezing and thawing the liquid pharmaceutical formulation, for example the antibody can be stable after one, two, three, four, five or more freeze/thaw cycles.

In one embodiment, the formulation is liquid and is stored as a single dose in one container, e.g., vial, syringe, cartridge, and/or autoinjector. The container can be stored at about 2-8° C. or 25° C. until it is administered to a subject in need thereof. The vial may for example be a 5, 10 or 20 cc vial (for example for a 108 mg dose at a volume of 1 mL or less). The vial may contain at least about 20 mg, at least about 50 mg, at least about 70 mg, at least about 80 mg, at least about 100 mg, at least about 120 mg, at least about 155 mg, at least about 180 mg, at least about 200 mg, at least about 240 mg, at least about 300 mg, at least about 360 mg, at least about 400 mg, at least about 540 mg, or at least about 900 mg of anti-alpha4beta7 antibody. In one aspect, the container contains about 108 mg of anti-alpha4beta7 antibody.

In another embodiment, the formulation is liquid and stored as a single dose in one or two vials, cartridges, syringes, or autoinjectors.

The vial, cartridge, syringe, or autoinjector can be stored at about 2-8° C. until its contents, e.g., an anti-alpha4beta7 antibody, are administered to a subject in need thereof. The vial may, for example, be a 5, 10 or 20 cc vial (for example for a 160 mg/ml dose). The vial may contain at least about 20 mg, at least about 50 mg, at least about 70 mg, at least about 80 mg, at least about 100 mg, at least about 120 mg, at least about 155 mg, at least about 180 mg, at least about 200 mg, at least about 240 mg, at least about 300 mg, at least about 360 mg, at least about 400 mg, at least about 540 mg, or at least about 900 mg of anti-alpha4beta7 antibody. In one aspect, the vial contains about 165 mg of anti-alpha4beta7 antibody. The syringe or cartridge may be a 1 mL or 2 mL container (for example for a 108 mg dose) or more than 2 ml, e.g., for a higher dose (216 mg. 300 mg, at least 320 mg or 400 mg or higher). The syringe or cartridge may contain at least about 20 mg, at least about 50 mg, at least about 70 mg, at least about 80 mg, at least about 100 mg, 100 mg to 108 mg, at least about 120 mg, at least about 155 mg, at least about 180 mg, at least about 200 mg, at least about 240 mg, at least about 300 mg, at least about 360 mg, at least about 400 mg, or at least about 500 mg of anti-alpha4beta7 antibody.

III. Humanized Alpha4Beta7Antibodies

Anti-alpha4beta7antibodies suitable for use in the formulations include an anti-alpha4beta7 antibody that can bind to an epitope on the alpha4 chain (e.g., humanized MAb 21.6 (Bendig et al., U.S. Pat. No. 5,840,299)), on the beta7 chain (e.g., FIB504 or a humanized derivative (e.g., Fong et al., U.S. Pat. No. 7,528,236)), or to a combinatorial epitope formed by the association of the alpha 4 chain with the beta 7 chain. In one aspect, the antibody binds a combinatorial epitope on the alpha4beta7complex, but does not bind an epitope on the alpha 4 chain or the beta 7 chain unless the chains are in association with each other. The association of alpha 4 integrin with beta 7 integrin can create a combinatorial epitope for example, by bringing into proximity residues present on both chains which together comprise the epitope or by conformationally exposing on one chain, e.g., the alpha4 integrin chain or the beta7 integrin chain, an epitopic binding site that is inaccessible to antibody binding in the absence of the proper integrin partner or in the absence of integrin activation. In another aspect, the anti-alpha4beta7 antibody binds both the alpha 4 integrin chain and the beta 7 integrin chain, and thus, is specific for the alpha4beta7integrin complex. Such antibodies can bind alpha4beta7but not bind alpha4beta1, and/or not bind alpha-Ebeta7, for example. In another aspect, the anti-alpha4beta7 antibody binds to the same or substantially the same epitope as the Act-1 antibody (Lazarovits, A. I. et al., J. Immunol., 133 (4): 1857-1862 (1984), Schweighoffer et al., J. Immunol., 151 (2): 717-729, 1993; Bednarczyk et al., J. Biol. Chem., 269 (11): 8348-8354, 1994). Murine ACT-1 Hybridoma cell line, which produces the murine Act-1 monoclonal antibody, was deposited under the provisions of the Budapest Treaty on Aug. 22, 2001, on behalf of Millennium Pharmaceuticals, Inc., 40 Landsdowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-alpha4beta7 antibody is a human antibody or an alpha4beta7 binding protein using the CDRs provided in U.S. Patent Application Publication No. 2010/0254975.

In one aspect, the anti-alpha4beta7 antibody inhibits binding of alpha4beta7 to one or more of its ligands (e.g. the mucosal addressin, e.g., MAdCAM (e.g., MAdCAM-1), fibronectin, and/or vascular addressin (VCAM)). Primate MAdCAMs (e.g., MAdCAM-1) are described in the PCT publication WO 96/24673, the entire teachings of which are incorporated herein by this reference. In another aspect, the anti-alpha4beta7 antibody inhibits binding of alpha4beta7 to MAdCAM (e.g., MAdCAM-1) and/or fibronectin without inhibiting the binding of VCAM.

In one aspect, the anti-alpha4beta7antibodies for use in the formulations are humanized versions of the mouse Act-1 antibody. Suitable methods for preparing humanized antibodies are well-known in the art. Generally, the humanized anti-alpha4beta7 antibody will contain a heavy chain that contains the 3 heavy chain complementarity determining regions (CDRs, CDR1, SEQ ID NO: 2, CDR2, SEQ ID NO:3 and CDR3, SEQ ID NO:4) of the mouse Act-1 antibody and suitable human heavy chain framework regions; and also contain a light chain that contains the 3 light chain CDRs (CDR1, SEQ ID NO:6, CDR2, SEQ ID NO:7 and CDR3, SEQ ID NO:8) of the mouse Act-1 antibody and suitable human light chain framework regions. The humanized Act-1 antibody can contain any suitable human framework regions, including consensus framework regions, with or without amino acid substitutions. For example, one or more of the framework amino acids can be replaced with another amino acid, such as the amino acid at the corresponding position in the mouse Act-1 antibody. The human constant region or portion thereof, if present, can be derived from the kappa or lamda light chains, and/or the gamma. (e.g., gamma1, gamma2, gamma3, gamma4), mu, alpha (e.g., alpha1, alpha2), delta or epsilon heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference.

In some embodiments, the anti-alpha4beta7 humanized antibodies for use in the formulation comprise a heavy chain variable region that has about 95%, 96%, 97%, 98%, or 99% sequence identity to SEQ ID NO: 1, and a light chain variable region that has about 95%, 96%, 97%, 98%, or 99% sequence identity to SEQ ID NO:2. Amino acid sequence identity can be determined using a suitable sequence alignment algorithm, such as the Lasergene system (DNASTAR, Inc., Madison, Wis.), using the default parameters. In an embodiment, the anti-alpha4beta7 antibody for use in the formulation is vedolizumab (CAS, American Chemical Society, Registry number 943609-66-3).

In one embodiment, an anti-alpha4beta7 antibody used in the liquid pharmaceutical formulations described herein comprises a heavy chain variable region as set forth in SEQ ID NO: 1, and a light chain variable region as set forth in SEQ ID NO: 5.

In one embodiment, an anti-alpha4beta7 antibody used in the liquid pharmaceutical formulations described herein is vedolizumab (ENTYVIO®). The amino acid sequences of vedolizumab are described in U.S. Pat. No. 9,764,033, which is incorporated by reference herein.

The anti-alpha4beta7 antibody can be produced by expression of nucleic acid sequences encoding each chain in living cells, e.g., cells in culture. A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an anti-alpha4beta7 antibody in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). For example, mammalian cells such as Chinese hamster ovary cells (CHO), in conjunction with a vector such as the major intermediate early gene promoter element from human cytomegalovirus, is an effective expression system for antibodies (Foecking et al., Gene 45:101 (1986); Cockett et al., Bio/Technology 8:2 (1990)).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to Chinese hamster ovary (CHO), NS0, HeLa, VERY, baby hamster kidney (BHK), monkey kidney (COS), MDCK, 293, 3T3, WI38, human hepatocellular carcinoma cells (e.g., Hep G2), breast cancer cell lines such as, for example, BT483, Hs578T, HTB2, BT20 and T47D, and normal mammary gland cell line such as, for example, CRL7030 and Hs578Bst.

The glycosylation machinery of different cell types can produce antibodies with different glycosylation composition than in another cell type, or no glycosylation, as with bacterial cells. In one aspect, cell types for production of the anti-alpha4beta7 antibody are mammalian cells, such as NS0 or CHO cells. In one aspect, the mammalian cells can comprise the deletion of an enzyme involved in cell metabolism and the exogenous gene of interest can be operably linked to a replacement enzyme, e.g., in a construct or vector for introduction into the cells, e.g., by transformation or transfection. The construct or vector with the exogenous gene confers to the cells which host the construct or vector a selection advantage to encourage production of the polypeptide encoded by the exogenous gene. In one embodiment, CHO cells are DG44 cells (Chasin and Urlaub (1980) PNAS USA 77:4216), comprising the deletion or inactivation of the dihydrofolate reductase gene. In another embodiment, CHO cells are CHO K1 cells comprising the deletion or inactivation of the glutamine synthase gene (see, e.g., U.S. Pat. No. 5,122,464 or 5,827,739).

IV. Delivery Devices

The liquid pharmaceutical formulations described herein can be used in with a delivery device suitable for subcutaneous delivery to a human subject. In one embodiment, the delivery device is a prefilled syringe. A prefilled syringe may be used as a delivery device alone or in combination with an autoinjector. Examples of delivery devices that may be used to deliver formulations described herein are known in the art and further provided below.

Liquid pharmaceutical formulations described herein can be used in a delivery device, e.g., an autoinjector having appropriate force to effectively deliver the antibody to a human patient. In particular, formulations described herein have both high concentrations (e.g., 90 mg/ml or more of antibody) and suitable viscosity for self-administration by the human subject in need thereof (e.g., having an inflammatory bowel disease) via an autoinjector. In particular, the formulation comprising the therapeutically effective amount of the humanized anti-alpha4beta7 antibody (e.g., vedolizumab) is placed in a pre-filled syringe which is then housed within an autoinjector having the capacity to effectively and safely deliver the formulation to a human subject in need thereof, particularly such that the human subject can self-administer the alpha4beta7 antibody.

An example autoinjector can be used in combination with a standard pre-filled syringe. The syringe can be assembled within a syringe holder of the autoinjector, and can have a substantially circular cross section. The syringe can be made of glass in order to ensure reliable and hygienic storing of the drug in the syringe. In a non-limiting example, a proximal end of the syringe has a reduced outer diameter or neck portion, at which a needle and needle shield are attached before delivery of the syringe. In order to ensure that the needle remains sterilized before use, the needle is protected by the needle shield having a substantially circular cross section and having an outer diameter which is larger than the outer diameter of the elongated syringe. The tubular needle shield encloses the needle and can be removably fastened to the syringe at the neck portion. The distal end of the tube-shaped syringe, opposite the proximal end, is arranged with a radially extending flange. The syringe also includes a movable plunger arranged in the distal end of the syringe to seal the syringe and ensure that the pre-filled drug of the syringe remains in the syringe. The movable plunger is can be made of a rubber material in order to achieve a seal between the inner periphery of the syringe and the plunger.

The syringe can be secured in the autoinjector housing using a syringe holder that is configured to support and maintain the syringe in a pre-determined position in relation to the syringe holder and the autoinjector housing. The syringe holder can have a substantially tubular shape and can fit within the autoinjector housing. The syringe holder can also include guiding means, such as corresponding longitudinal protrusions along the outer periphery of the syringe holder and/or longitudinal recesses along the inner periphery of the autoinjector housing, in order to guide movement of the syringe holder within the autoinjector housing. In a non-limiting example, snap-fitting fasteners can be arranged on the syringe holder in order to secure the syringe holder in a desired position within the autoinjector housing. In a non-limiting example, the autoinjector housing includes a window, or opening, that can align with a slot or opening in the syringe holder when the syringe holder is fitted in the intended position within the autoinjector housing in order to make the syringe, and the drug in the syringe, visible to a user.

In a non-limiting example, the syringe also includes a resilient member, such as a tension spring, configured to engage a portion of a plunger rod and expel the medicament or drug from the syringe when the autoinjector is activated. The resilient member can be configured to apply a force between about 1-10 Newtons (N), about 2-20 N, about 3-17 N, about 4-15 N, about 5-10 N, about 2-9 N, about 5-8 N, about 7-13 N or about 10 N to the plunger rod in the proximal direction. In some embodiments, various characteristics of the resilient member can be selected or adjusted in order to exert the desired amount of force during activation of the autoinjector. Example characteristics can include, for example, spring thickness, number of coils in a compression spring, material strength, etc. In some embodiments, the amount and/or timing of the force applied by the resilient member to the plunger can depend, at least in part, on the viscosity of the medicament or drug being delivered.

In some embodiments, example autoinjectors and autoinjector components can include one or more of the devices or components described in U.S. Pat. Nos. 9,867,940, 9,199, 038, 9,220,841, 9,662,452, 8,821,451, 9,216,251, 10,092, 704, 9,713,677, 10,130,774; U.S. Patent Publication Nos. 2016/0089498, 2017/0209647, 2018/0318514, 2018/0064875, 2016/0213845, 2018/0333536; each of which are incorporated herein by reference in their entirety with respect to the delivery devices disclosed therein.

In some embodiments, example autoinjectors or injection devices and related components can also include one or more of the following devices or components described in U.S. Pat. Nos. 7,207,973, 6,776,777, 7,390,312, 7,041,092, each of which are incorporated herein by reference in their entirety with respect to the autoinjectors, injection devices and related components disclosed therein.

In some example embodiments, example injection devices and related components can also include one or more of the following devices or components described in U.S. Pat. No. 9,248,242, which is incorporated herein by reference in its entirely with respect to the injection device and related components disclosed therein.

It should be appreciated by those of skill in the art that there are numerous autoinjectors that can be used with the formulations described herein. In some embodiments, the autoinjector described in U.S. Pat. No. 8,821,451, which has been incorporated herein in its entirety, can be used with the liquid pharmaceutical formulations taught herein (see, e.g., FIGS. 1A-5 and corresponding text of U.S. Pat. No. 8,821, 451). In some embodiments, the autoinjector can include a physical firing button that can be depressed using a finger or thumb of the user to initiate and complete injection of the formulation. In some embodiments, the autoinjector can be provided an activation element in place of a firing button. For example, a tubular activation element or other shaped activation element that can be positioned against the injection site and pressed downwardly to initiate injection without depression of a firing button.

In some embodiments, an injection aide or tool described in U.S. Pat. No. 9,248,242, which has been incorporated herein in its entirety, can be used with the liquid pharmaceutical formulations taught herein (see, e.g., FIGS. 1-29 and corresponding text of U.S. Pat. No. 9,248,242). The injection aide or tool is a device that allows the use to physically depress a plunger rod to make an injection, but provides some form of automatic needle shield deployment system that automatically deploys a needle shield to provide protection against accidental needle pricks post injection.

Another exemplary injection aide or tool for use with the formulations taught herein includes the injection aide or tool as described in U.S. Pat. No. 7,207,973, which has been incorporated herein in its entirety (see, e.g., FIGS. 1-12 and corresponding text of U.S. Pat. No. 7,207,973). The injection aide or tool includes a safety shield that allows the user to inject the formulation, and ensures that the needle is shielded following removal of the syringe from the injection site.

Additional example autoinjectors and autoinjector components that can be used in combination with a liquid pharmaceutical formulation described herein, include one or more of the devices or components described in U.S. Pat. Nos. 8,529,510, 8,808,244, 9,248,236, 9,468,723, and 10166336; and International Patent Publication No. WO 2011/005177, each of which is incorporated herein by reference in its entirety.

In exemplary embodiments, the autoinjector can include a housing portion that may be made of any number of materials including plastics. The housing portion can include an upper and lower housing component, or may be one unified component. The autoinjector may include an activation mechanism, such as a firing button, that can be activated in order to deliver a drug or medicament through a needle of a syringe held within the autoinjector. The autoinjector may also include a removable needle cap that can be removed prior to operation of the autoinjector. In some embodiments, the activation mechanism can be a button which may be rotated to lock or unlock the device and depressed to activate the device. In some embodiments, the activation mechanism can be placed against the injection site and depressed to activate the device. Upon depression of the activation mechanism, a syringe held within the autoinjector can be activated to deliver a drug or medicament. In some example embodiments, the needle of the syringe can retract once delivery of the drug is completed. The autoinjector housing may optionally contain one or more transparent or translucent windows to enable a user to view the operation of the autoinjector or verify that a drug dose has completed. In some embodiments, the autoinjector can include a needle shield that may surround or cover a portion of the syringe needle.

In another aspect, the invention is an article of manufacture which contains the delivery device containing a formulation described herein and provides instructions for its use. The article of manufacture comprises a container. Suitable containers include, for example, bottles, vials (e.g., dual chamber vials, a vial of liquid formulation with or without a needle), syringes (such as dual chamber syringes, preloaded syringes, an auto-injector), cartridges, and test tubes. The container may be formed from a variety of materials such as glass, metal or plastic. The container holds the formulation and a label on, or associated with, the container may indicate directions for use. In another embodiment, the formulation can be prepared for self-administration and/or contain instructions for self-administration. In one aspect, the container holding the formulation may be a single-use vial. In another aspect, the container holding the formulation may be a multi-use vial, which allows for repeat administration (e.g., from 2-6 administrations) of the formulation, e.g., using more than one portion of a reconstituted formulation. The article of manufacture may further include other materials desirable from a commercial and user standpoint, including other buffers, diluents, filters, needles, syringes and package inserts with instructions for use as noted in the previous section.

A pre-filled syringe can be injected manually or used with an auto-injector device. Functional testing of the pre-filled syringe includes measuring the breakloose force, the force required to begin movement of the plunger, and the gliding force, the force needed to inject the contents of the syringe at a constant rate. The mechanical performance of the pre-filled syringe can be dependent on several formulation and syringe parameters such as the viscosity of the formulation and the amount of lubricant (e.g., silicone oil) in the syringe.

In one embodiment, the prefilled syringe has a needle. The gauge of the needle may be 25 G, 26 G, 27 G, 29 G, or 30 G. A thin wall needle, e.g., 19 G or 23 G, or greater, can facilitate injection of a high viscosity formulation. In one aspect, the needle gauge is 27 G. Needle length can also be suitable for subcutaneous administration of a pharmaceutical formulation, and can be about ½ inch, about ⅝ inch or 1 inch long. In some embodiments, the needle of the syringe can include three bevels at the tip to reduce injection pain. In some embodiments, the needle of the syringe can include five bevels at the tip to reduce injection pain.

In one embodiment, the autoinjector contains a prefilled syringe having a 27 G ½ needle. Further, the syringe may be glass.

FIG. 1 graphically depicts the impact of temperature on viscosity of vedolizumab at various concentrations of an exemplary anti-alpha4beta7 antibody formulation. Most liquid pharmaceutical formulations are stored in a refrigerator until ready for use, with the liquid pharmaceutical formulation generally being removed from the refrigerator about 15 minutes to about an hour before injection in order to bring the liquid pharmaceutical formulation to substantially room temperature. As shown in FIG. 1, the viscosity of liquid pharmaceutical formulations is generally higher during refrigeration and reduces as the liquid pharmaceutical formulation is brought to or towards room temperature. If a user fails to remove a liquid pharmaceutical formulation from refrigeration prior to injection or fails to wait until the liquid pharmaceutical formulation reaches room temperature, the higher viscosity of the liquid pharmaceutical formulation can result in an unsuccessful injection.

To prevent or reduce unsuccessful injections when the liquid pharmaceutical formulation is at an elevated viscosity (as compared to a liquid pharmaceutical formulation at room temperature), autoinjectors and syringes discussed herein can include a piston (e.g., stopper) having reduced breakloose and glide forces, resulting in improved injection of the formulation at a greater range of temperatures. Particularly, the reduced breakloose and glide forces increase the likelihood of successful injections of formulations even at formulation temperatures below room temperature.

Figure 2:
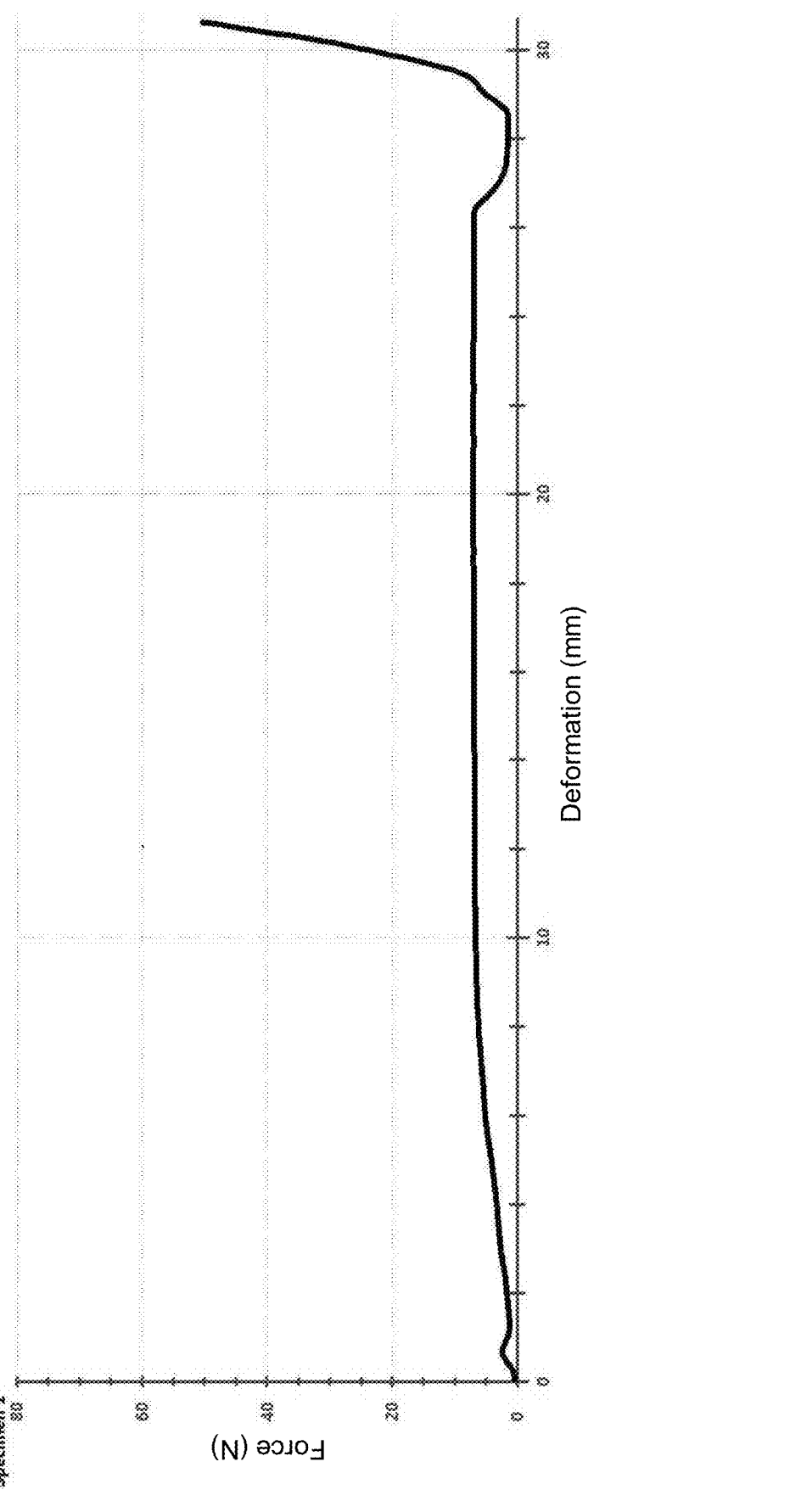
FIG. 2 graphically depicts breakloose force and glide force relative to deformation and force.

FIG. 2 graphically depicts breakloose force and glide force relative to deformation (e.g., compressive extension) and force (e.g., compressive loading force). The force is shown in N and the deformation is shown in mm. The breakloose force, as used herein, refers to a force required to start the plunger moving in an autoinjector or injection device. The glide force, as used herein, refers to a friction of the plunger as the plunger moves through the shaft of the autoinjector or injection device. The piston (e.g., stopper) for the autoinjector can be selected based on a configuration that reduces the breakloose and glide forces.

Figure 3:
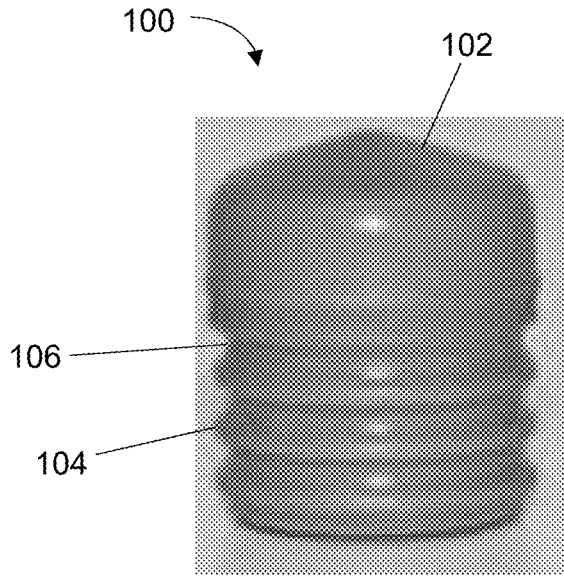
FIG. 3 is a side view of a first embodiment of a piston for an autoinjector.
Figure 4:
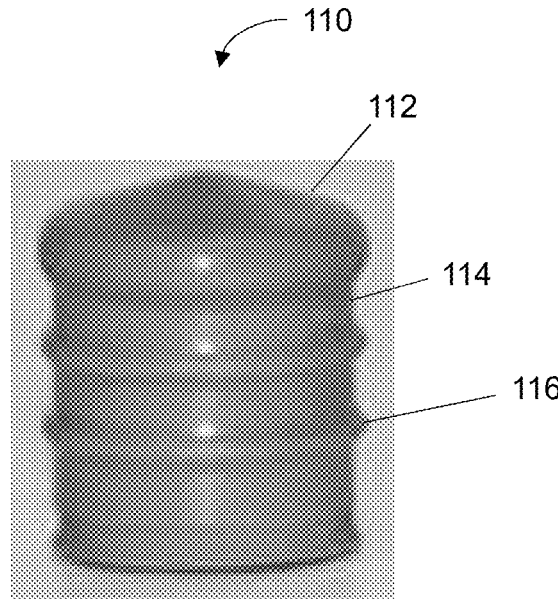
FIG. 4 is a side view of a second embodiment of a piston for an autoinjector.

FIGS. 3 and 4 are side views of first and second embodiments of pistons 100, 110 for an autoinjector. The piston 100 can be an Art2340 piston, and the piston 110 can be a NovaPure® piston. In some embodiments, the pistons 100, 110 can include a top surface 102, 112 covered by a film having a low friction coefficient, e.g., a FluroTec® film. The film covering the top surface 102, 112 can extend downwardly along the side surfaces of the piston or can extend just over the edge of the top surface 102, 112 without significantly covering the side surfaces of the piston. In some embodiments, the piston 100 can include three circumferential ribs 104 disposed between the top and bottom surfaces of the piston 100. In some embodiments, the piston 110 can include two circumferential ribs 114 disposed between the top and bottom surfaces of the piston 110. The ribs 104, 114 can be separated by circumferential grooves 106, 116. The pistons 100, 110 can include a low friction coefficient coating over the side surfaces and/or ribs 104, 114 to facilitate improved movement and/or sliding of the piston during injection. The pistons 100, 110 thereby reduce the breakloose and glide forces associated with injection of a formulation.

In some embodiments, the maximum breakloose force for a 160 mg/mL concentration can be about 3.16 N, and for a 176 mg/mL concentration can be about 3.16 N. In some embodiments, the breakloose force for a 160 mg/mL concentration can be in a range of about 2.04 N to about 3.16 N, and for a 176 mg/mL concentration can be in a range of about 2.02 N to about 3.16 N. In some embodiments, the maximum glide force for a 160 mg/mL concentration can be about 8.11 N, and for a 176 mg/mL concentration can be about 11.56 N. In some embodiments, the glide force for a 160 mg/mL concentration can be in a range of about 6.16 N to about 8.11 N, and for a 176 mg/mL concentration can be in a range of about 8.38 N to about 11.56 N.

In some embodiments, the needle bevel can be changed to reduce the injection pain (e.g., 27 G ½" with same inner and outer dimensions).

In some embodiments, the rigid needle shield design can be changed to accommodate an autoinjector design. The bevel and needle shield changes generally do not affect the breakloose and glide forces.

V. Methods of Treatment

In one aspect, the invention provides a method of treating a disease or disorder in a subject comprising administering to a subject the anti-alpha4beta7 antibody liquid pharmaceutical formulation described herein providing an effective amount of the antibody to treat the disease or disorder, e.g., in humans. The human subject may be an adult (e.g., 18 years or older), an adolescent, or a child. The human subject may be a person 65 years or older. In contrast to alternative therapeutic dosing regimens, a human subject 65 years or older does not require any modification of the dosing regimen described herein, and may be administered the conventional anti-alpha4beta7 antibody liquid pharmaceutical formulation described herein.

In one embodiment, the liquid pharmaceutical formulations described herein are used to treat a subject may have had a lack of an adequate response with, loss of response to, or was intolerant to treatment with an immunomodulator, a TNF-alpha antagonist, or combinations thereof. The patient may have previously received treatment with at least one corticosteroid (e.g., prednisone) and had an inadequate response with, were intolerant to, or demonstrated dependence on corticosteroids for the inflammatory bowel disease. An inadequate response to corticosteroids refers to signs and symptoms of persistently active disease despite a history of at least one 4-week induction regimen that included a dose equivalent to prednisone 30 mg daily orally for 2 weeks or intravenously for 1 week. A loss of response to corticosteroids refers to two failed attempts to taper corticosteroids to below a dose equivalent to prednisone 10 mg daily orally. Intolerance of corticosteroids includes a history of Cushing's syndrome, osteopenia/osteoporosis, hyperglycemia, insomnia and/or infection.

An immunomodulator may be, for example, oral azathioprine, 6-mercaptopurine, or methotrexate. An inadequate response to an immunomodulator refers to signs and symptoms of persistently active disease despite a history of at least one 8 week regimen or oral azathioprine (greater than or equal to 1.5 mg/kg), 6-mercaptopurine (greater than or equal to 0.75 mg/kg), or methotrexate (greater than or equal to 12.5 mg/week). Intolerance of an immunomodulator includes, but is not limited to, nausea/vomiting, abdominal pain, pancreatitis, LFT abnormalities, lymphopenia. TPMT genetic mutation and/or infection.

A TNFalpha antagonist is, for example, an agent that inhibits the biological activity of TNFalpha, and preferably binds TNFalpha, such as a monoclonal antibody, e.g., REMICADE (infliximab), HUMIRA (adalimumab), CIMZIA (certolizumab pegol), SIMPONI (golimumab) or a circulating receptor fusion protein such as ENBREL (etanercept). An inadequate response to a TNF-alpha antagonist refers to signs and symptoms of persistently active disease despite a history of at least one 4 week induction regimen of infliximab 5 mg/kg IV, 2 doses at least 2 weeks apart; one 80 mg subcutaneous dose of adalimumab, followed by one 40 mg dose at least two weeks apart; or 400 mg subcutaneously of certolizumab pegol, 2 doses at least 2 weeks apart. A loss of response to a INF-alpha antagonist refers to recurrence of symptoms during maintenance dosing following prior clinical benefit. Intolerance of a TNFalpha antagonist includes, but is not limited to infusion related reaction, demyelination, congestive heart failure, and/or infection.

A loss of maintenance of remission, as used herein for ulcerative colitis subjects, refers to an increase in Mayo score of at least 3 points and a Modified Baron Score of at least 2.

In another aspect, the present invention provides liquid pharmaceutical formulations containing an effective amount of an anti-alpha4beta7 antibody which (1) can bind alpha4beta7integrin in vitro and/or in vivo; and (2) can modulate an activity or function of an alpha4beta7integrin, such as (a) binding function (e.g., the ability of alpha4beta7integrin to bind to MAdCAM (e.g., MAdCAM-1), fibronectin and/or VCAM-1) and/or (b) leukocyte infiltration function, including recruitment and/or accumulation of leukocytes in tissues (e.g., the ability to inhibit lymphocyte migration to intestinal mucosal tissue). In one embodiment, an antibody in the liquid pharmaceutical formulation can bind an alpha4beta7integrin, and can inhibit binding of the alpha4beta7integrin to one or more of its ligands (e.g., MAdCAM (e.g., MAdCAM-1), VCAM-1, fibronectin), thereby inhibiting leukocyte infiltration of tissues (including recruitment and/or accumulation of leukocytes in tissues). In another embodiment, an antibody in the liquid pharmaceutical formulation can bind an alpha4beta7integrin, and can selectively inhibit binding of the alpha4beta7integrin to one or more of its ligands (e.g., MAdCAM (e.g., MAdCAM-1), VCAM-1, fibronectin), thereby inhibiting leukocyte infiltration of tissues (including recruitment and/or accumulation of leukocytes in tissues). Such an anti-alpha4beta7 antibody in a liquid pharmaceutical formulation described herein can inhibit cellular adhesion of cells bearing an alpha4beta7integrin to vascular endothelial cells in mucosal tissues, including gut-associated tissues, lymphoid organs or leukocytes (especially lymphocytes such as T or B cells) in vitro and/or in vivo. In yet another embodiment, the anti-alpha4beta7 antibody in the liquid pharmaceutical formulation of the present invention can inhibit the interaction of alpha4beta7 with MAdCAM (e.g., MAdCAM-1) and/or fibronectin. In still yet another embodiment, the anti-alpha4beta7 antibody in the liquid pharmaceutical formulation of the present invention can inhibit the interaction of alpha4beta7 with MAdCAM (e.g., MAdCAM-1) and/or fibronectin selectively, e.g., without inhibiting the interaction of alpha4beta7 with VCAM.

The anti-alpha4beta7 antibody liquid pharmaceutical formulations of the present invention can be used to deliver the antibody such that it can modulate (e.g., inhibit (reduce or prevent)) binding function and/or leukocyte (e.g., lymphocyte, monocyte) infiltration function of alpha4beta7integrin. For example, humanized immunoglobulins which inhibit the binding of alpha4beta7integrin to a ligand (i.e., one or more ligands) can be administered according to the method in the treatment of diseases associated with leukocyte (e.g., lymphocyte, monocyte) infiltration of tissues (including recruitment and/or accumulation of leukocytes in tissues), particularly of tissues which express the molecule MAdCAM (e.g., MAdCAM-1).

An effective amount of an anti-alpha4beta7 antibody is administered in a liquid pharmaceutical formulation described herein to an individual (e.g., a mammal, such as a human or other primate) in order to treat such a disease. For example, inflammatory diseases, including diseases which are associated with leukocyte infiltration of the gastrointestinal tract (including gut-associated endothelium), other mucosal tissues, or tissues expressing the molecule MAdCAM (e.g., MAdCAM-1) (e.g., gut-associated tissues, such as venules of the lamina propria of the small and large intestine; and mammary gland (e.g., lactating mammary gland)), can be treated according to the present method. Similarly, an individual having a disease associated with leukocyte infiltration of tissues as a result of binding of leukocytes to cells (e.g., endothelial cells) expressing MAdCAM (e.g., MAdCAM-1) can be treated according to the present invention.

In one embodiment, diseases which can be treated accordingly include inflammatory bowel disease (IBD), such as ulcerative colitis, Crohn's disease, ileitis, Celiac disease, nontropical Sprue, enteropathy associated with seronegative arthropathies, microscopic or collagenous colitis, eosinophilic gastroenteritis, or pouchitis resulting after proctocolectomy, and ileoanal anastomosis. In some embodiments, the inflammatory bowel disease is Crohn's disease or ulcerative colitis.

Ulcerative colitis may be moderate to severely active ulcerative colitis (e.g., having a Mayo score of six to 12 with endoscopy subscore of two or three). Treatment may result in induction and maintenance of clinical response, induction and maintenance of clinical remission, or mucosal healing in patients suffering from moderate to severely active ulcerative colitis. Treatment may also result in a reduction, elimination, or reduction and elimination of corticosteroid use by the patient (e.g., corticosteroid-free remission).

Crohn's disease may be moderate to severely active Crohn's disease (e.g., Crohn's Disease Activity Index (CDAI) score 220 to 450). Treatment may achieve clinical response or achieve clinical remission in patients suffering from moderate to severely active Crohn's disease. Treatment may also result in a reduction, elimination, or reduction and elimination of corticosteroid use by the patient (e.g., corticosteroid-free remission).

Pancreatitis and insulin-dependent diabetes mellitus are other diseases which can be treated using the formulations of the invention. It has been reported that MAdCAM (e.g., MAdCAM-1) is expressed by some vessels in the exocrine pancreas from NOD (nonobese diabetic) mice, as well as from BALB/c and SJL mice. Expression of MAdCAM (e.g., MAdCAM-1) was reportedly induced on endothelium in inflamed islets of the pancreas of the NOD mouse, and MAdCAM (e.g., MAdCAM-1) was the predominant addressin expressed by NOD islet endothelium at early stages of insulitis (Hanninen, A., et al., J. Clin. Invest., 92:2509-2515 (1993)). Treatment of NOD mice with either anti-MAdCAM or anti-beta 7 antibodies prevented the development of diabetes (Yang et al., Diabetes, 46:1542-1547 (1997)). Further, accumulation of lymphocytes expressing alpha4beta7within islets was observed, and MAdCAM-1 was implicated in the binding of lymphoma cells via alpha4beta7 to vessels from inflamed islets (Hanninen, A., et al., J. Clin. Invest., 92:2509-2515 (1993)) or to the gastrointestinal tract in mantle cell lymphoma (Geissmann et al., Am. J. Pathol., 153:1701-1705 (1998)).

Examples of inflammatory diseases associated with mucosal tissues which can be treated using a formulation of the invention include cholecystitis, cholangitis (Adams and Eksteen Nature Reviews 6:244-251 (2006) Grant et al., Hepatology 33:1065-1072 (2001)), e.g., primary sclerosing cholangitis, Behcet's disease, e.g., of the intestine, or pericholangitis (bile duct and surrounding tissue of the liver), and graft versus host disease (e.g., in the gastrointestinal tract (e.g., after a bone marrow transplant) (Petrovic et al. Blood 103:1542-1547 (2004)). As seen in Crohn's disease, inflammation often extends beyond the mucosal surface, accordingly chronic inflammatory diseases, such as sarcoidosis, chronic gastritis, e.g., autoimmune gastritis (Katakai et al., Int. Immunol., 14:167-175 (2002)) and other idiopathic conditions can be amenable to treatment.

The invention also relates to a method of inhibiting leukocyte infiltration of mucosal tissue. The invention also relates to a method for treating cancer (e.g., an alpha4beta7positive tumor, such as a lymphoma). Other examples of inflammatory diseases associated with mucosal tissues which can be treated using a formulation of the invention include mastitis (mammary gland) and irritable bowel syndrome.

Diseases or pathogens whose etiologies exploit the interaction of MAdCAM (e.g., MAdCAM-1) with alpha4beta7 can be treated with an anti-alpha4beta7 antibody in a formulation described herein. Examples of such diseases include immunodeficiency disorders, such as caused by human immunodeficiency virus (Sec, e.g., WO2008140602).

A liquid pharmaceutical formulation of the invention is administered in an effective amount which inhibits binding of alpha4beta7integrin to a ligand thereof. For therapy, an effective amount will be sufficient to achieve the desired therapeutic (including prophylactic) effect (such as an amount sufficient to reduce or prevent alpha4beta7integrin-mediated binding and/or signaling, thereby inhibiting leukocyte adhesion and infiltration and/or associated cellular responses). An effective amount of an anti-alpha4beta7 antibody, e.g., an effective titer sufficient to maintain saturation, e.g., neutralization, of alpha4beta7integrin, can induce clinical response or remission in inflammatory bowel disease. An effective amount of an anti-alpha4beta7 antibody can lead to mucosal healing in ulcerative colitis or Crohn's disease. A formulation of the invention can be administered in a unit dose or multiple doses. The dosage can be determined by methods known in the art and can be dependent, for example, upon the individual's age, sensitivity, tolerance and overall well-being. Examples of modes of administration include topical routes such as nasal or inhalational or transdermal administration, enteral routes, such as through a feeding tube or suppository, and parenteral routes, such as intravenous, intramuscular, subcutaneous, intraarterial, intraperitoneal, or intravitreal administration. Suitable dosages for antibodies can be from about 0.1 mg/kg body weight to about 10.0 mg/kg body weight per treatment, for example about 2 mg/kg to about 7 mg/kg, about 3 mg/kg to about 6 mg/kg, or about 15 to about 5 mg/kg. In particular embodiments, the dose administered is about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. The total dose may be about 22 mg, about 50 mg, about 72 mg, about 125 mg, about 165 mg, or about 432 mg. The total dose may be at least 77 mg, at least 125 mg or at least 356 mg. In one embodiment, the total dose is 165 mg. In another embodiment, the total dose is 108 mg. In another embodiment, the total dose is 216 mg. In another embodiment, the total dose is 300 mg.

In some aspects, the dosing regimen for treating a disease described herein, e.g., UC or Crohn's, has two phases, an induction phase and a maintenance phase. In the induction phase, the antibody or antigen-binding fragment thereof is administered in a way that quickly provides an effective amount of the antibody or antigen binding fragment thereof suitable for certain purposes, such as inducing immune tolerance to the antibody or antigen-binding fragment thereof or for inducing a clinical response and ameliorating inflammatory bowel disease symptoms. A patient can be administered an induction phase treatment when first being treated by an anti-alpha4beta7 antibody, when being treated after a long absence from therapy, e.g., more than three months, more than four months, more than six months, more than nine months, more than one year, more than eighteen months or more than two years since anti-alpha4beta7 antibody therapy or during maintenance phase of anti-alpha4beta7 antibody therapy if there has been a return of inflammatory bowel disease symptoms, e.g., a relapse from remission of disease. In some embodiments, the induction phase regimen results in a higher mean trough serum concentration, e.g., the concentration just before the next dose, than the mean steady state trough serum concentration maintained during the maintenance regimen.

In the maintenance phase, the antibody or antigen-binding fragment thereof is administered in a way that continues the response achieved by induction therapy with a stable level of antibody or antigen-binding fragment thereof. A maintenance regimen can prevent return of symptoms or relapse of inflammatory bowel disease. A maintenance regimen can provide convenience to the patient, e.g., be a simple dosing regimen or require infrequent trips for treatment. In some embodiments, the maintenance regimen can include administration of the anti-alpha4beta7 antibody or antigen-binding fragment thereof, e.g., in a formulation described herein, by a strategy selected from the group consisting of low dose, infrequent administration, self-administration and a combination any of the foregoing.

In one embodiment, e.g., during an induction phase of therapy, the dosing regimen provides an effective amount of an anti-alpha4beta7 antibody or antigen-binding fragment in a formulation described herein for inducing remission of an inflammatory bowel disease in a human patient. The duration of induction phase can be about four weeks, about five weeks, about six weeks, about seven weeks, or about eight weeks of treatment. In some embodiments, the induction regimen can utilize a strategy selected from the group consisting of high dose, frequent administration, and a combination of high dose and frequent administration of the anti-alpha4beta7 antibody or antigen-binding fragment thereof, e.g., in a formulation described herein. Induction dosing can be once, or a plurality of more than one dose, e.g., at least two doses. During induction phase, a dose can be administered once per day, every other day, twice per week, once per week, once every ten days, once every two weeks or once every three weeks. In some embodiments, the induction doses are administered within the first two weeks of therapy with the anti-alpha4beta7 antibody. In one embodiment, induction dosing can be once at initiation of treatment (day 0) and once at about two weeks after initiation of treatment. In another embodiment, the induction phase duration is six weeks. In another embodiment, the induction phase duration is six weeks and a plurality of induction doses are administered during the first two weeks.

In some embodiments, e.g., when initiating treatment of a patient with severe inflammatory bowel disease (e.g., in patients who have failed anti-TNFalpha therapy), the induction phase needs to have a longer duration than for patients with mild or moderate disease. In some embodiments, the induction phase for a patient with a severe disease can have a duration of at least 6 weeks, at least 8 weeks, at least 10 weeks, at least 12 weeks or at least 14 weeks. In one embodiment, an induction dosing regimen for a patient with a severe disease can include a dose at week 0 (initiation of treatment), a dose at week 2 and a dose at week 6. In another embodiment, an induction dosing regimen for a patient with a severe disease can comprise a dose at week 0 (initiation of treatment), a dose at week 2, a dose at week 6 and a dose at week 10.

The final dosage form for subcutaneous delivery via an autoinjector can comprise the entire dose in about 0.5 ml, in about 1 ml, in about 1.5 ml in about 2 ml, in about 2.5 ml, in about 3 ml of the antibody formulation.

The dose can be administered once per week, once every 2 weeks, once every 3 weeks, once every 4 weeks, once every 6 weeks, once every 8 weeks or once every 10 weeks. A higher or more frequent dose, e.g., every other day, once per week, once every 2 weeks, once every 3 weeks or once every 4 weeks can be useful for inducing remission of active disease or for treating a new patient, e.g., for inducing tolerance to the anti-alpha4beta7 antibody. A dose once every 2 weeks, once every 3 weeks, once every 4 weeks, once every 5 weeks, once every 6 weeks, once every 8 weeks or once every 10 weeks, can be useful for preventative therapy, e.g., to maintain remission of a patient with chronic disease. In one aspect, the treatment regimen is treatment at day 0, about week 2, about week 6 and every 1 or 2 weeks thereafter. In certain aspects, the treatment regimen is treatment at day 0, about week 2, about week 6 and every 8 weeks thereafter. In another aspect, the induction treatment regimen is treatment every other day for a total of 6 treatments.

The dosing regimen can be optimized to induce a clinical response and clinical remission in the inflammatory bowel disease of the patient. In some embodiments, the dosing regimen does not alter the ratio of CD4 to CD8 in cerebrospinal fluid of patients receiving treatment.

In some aspects, a durable clinical remission, for example, a clinical remission which is sustained through at least two, at least three, at least four visits with a caretaking physician within a six month or one year period after beginning treatment, may be achieved with an optimized dosing regimen.

In some aspects, a durable clinical response, for example, a clinical response which is sustained for at least 6 months, at least 9 months, at least a year, after the start of treatment, may be achieved with an optimized dosing regimen.

The formulation may be administered subcutaneously in single or multiple injections. For example, the volume of a single injection may range from about 0.5 ml to about 3 ml. In an embodiment, the volume of a single injection may be about 0.6 ml to about 1.1 ml or about 1 ml to about 3 mi. In one aspect, the volume of a single injection is about 1 ml. The gauge of the needle used to administer the formulation subcutaneously may be about 25, about 26, about 27, about 28, about 29 or about 30 G.

The formulation may be administered intramuscularly in single or multiple injections. For example, the volume of a single injection may range from about 0.5 ml to about 5 ml. In an embodiment, the volume of a single injection may be about 2 ml to about 5 ml, about 0.6 ml to about 1.1 ml or about 1 ml to about 3 ml. In one aspect, the volume of a single injection is about 1 ml, about 2 ml, about 3 ml, about 4 ml, or about 5 ml. The needle used to administer the formulation intramuscularly may be about ⅝", about ⅞", about 1", about 1.25", about 1.5", about 2", or about 3". The gauge of the needle may be between 20-22 G for intramuscular administration.

In one aspect, the invention relates to a method for treating a human patient suffering from inflammatory bowel disease, wherein the method comprises the step of administering to a patient suffering from inflammatory bowel disease, a humanized immunoglobulin or antigen-binding fragment thereof having binding specificity for human alpha4beta7integrin, wherein the humanized immunoglobulin or antigen-binding fragment thereof is administered to the patient according to the following dosing regimen: (a) initial doses of 165 mg of the humanized immunoglobulin or antigen-binding fragment thereof as a subcutaneous injection every other day for six doses; (b) followed by a seventh and subsequent doses of 165 mg of the humanized immunoglobulin or antigen-binding fragment thereof as a subcutaneous injection every two weeks or every four weeks as needed; wherein the dosing regimen induces a clinical response and clinical remission in the inflammatory bowel disease of the patient; and further wherein the humanized immunoglobulin or antigen-binding fragment has binding specificity for the alpha4beta7complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:6, CDR2 SEQ ID NO: 7, CDR3 SEQ ID NO:8; heavy chain: CDR1 SEQ ID NO:2, CDR2 SEQ ID NO:3, CDR3 SEQ ID NO:4.

In one aspect, the invention relates to a method for treating a human patient suffering from inflammatory bowel disease, wherein the method comprises the step of administering to a patient suffering from inflammatory bowel disease, a humanized immunoglobulin or antigen-binding fragment thereof having binding specificity for human alpha4beta7integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to the following dosing regimen: (a) an initial intravenous dose of 300 mg of the humanized immunoglobulin or antigen-binding fragment thereof as an intravenous infusion; (b) followed by a second intravenous subsequent dose of 300 mg of the humanized immunoglobulin or antigen-binding fragment thereof as an intravenous infusion at about two weeks after the initial dose; (c) followed beginning at week six by a third and subsequent doses of 165 mg of the humanized immunoglobulin or antigen-binding fragment thereof as a subcutaneous injection every week, every two weeks or every three weeks as needed; wherein the dosing regimen induces a clinical response and clinical remission in the inflammatory bowel disease of the patient; and further wherein the humanized immunoglobulin or antigen-binding fragment has binding specificity for the alpha4beta7complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:6, CDR2 SEQ ID NO: 7, CDR3 SEQ ID NO:8; heavy chain: CDR1 SEQ ID NO:2, CDR2 SEQ ID NO:3, CDR3 SEQ ID NO:4.

In another aspect, the invention relates to a dosing regimen for the therapeutic treatment of inflammatory bowel disease, wherein the dosing regimen comprises the step of: administering to a patient suffering from inflammatory bowel disease, a humanized immunoglobulin or antigen-binding fragment thereof having binding specificity for human alpha4beta7integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to a subcutaneous or intramuscular dosing regimen which maintains a mean steady state serum trough concentration of about 9 to about 13 μg/mL of the antibody or antigen-binding fragment thereof; wherein the dosing regimen induces a clinical response and clinical remission in the inflammatory bowel disease of the patient; and further wherein the humanized immunoglobulin or antigen-binding fragment has binding specificity for the alpha4beta7complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:6, CDR2 SEQ ID NO: 7, CDR3 SEQ ID NO:8; heavy chain: CDR1 SEQ ID NO:2, CDR2 SEQ ID NO:3, CDR3 SEQ ID NO:4.

In another aspect, the invention relates to a dosing regimen for the therapeutic treatment of inflammatory bowel disease, wherein the dosing regimen comprises the step of: administering to a patient suffering from inflammatory bowel disease, a humanized immunoglobulin or antigen-binding fragment thereof having binding specificity for human alpha4beta7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to a subcutaneous or intramuscular dosing regimen which maintains a steady state serum trough concentrations of about 35 to about 40 g/mL of the antibody or antigen-binding fragment thereof; wherein the dosing regimen induces a clinical response and clinical remission in the inflammatory bowel disease of the patient; and further wherein the humanized immunoglobulin or antigen-binding fragment has binding specificity for the alpha4beta7complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:6, CDR2 SEQ ID NO: 7, CDR3 SEQ ID NO:8; heavy chain: CDR1 SEQ ID NO:2, CDR2 SEQ ID NO:3, CDR3 SEQ ID NO:4.

The formulation may be administered to an individual (e.g., a human) alone or in conjunction with another agent. A liquid pharmaceutical formulation described herein can be administered before, along with or subsequent to administration of the additional agent. In one embodiment, more than one formulation which inhibits the binding of alpha4beta7integrin to its ligands is administered. In such an embodiment, an agent, e.g., a monoclonal antibody, such as an anti-MAdCAM or an anti-VCAM-1 monoclonal antibody can be administered. In another embodiment, the additional agent inhibits the binding of leukocytes to an endothelial ligand in a pathway different from the alpha4beta7pathway. Such an agent can inhibit the binding, e.g. of chemokine (C—C motif) receptor 9 (CCR9)-expressing lymphocytes to thymus expressed chemokine (TECK or CCL25) or an agent which prevents the binding of LFA-1 to intercellular adhesion molecule (ICAM). For example, an anti-TECK or anti-CCR9 antibody or a small molecule CCR9 inhibitor, such as inhibitors disclosed in PCT publication WO03/099773 or WO04/046092, or anti-ICAM-1 antibody or an oligonucleotide which prevents expression of ICAM, is administered in addition to a formulation of the present invention. In yet another embodiment, an additional active ingredient (e.g., an anti-inflammatory compound, such as sulfasalazine, azathioprine, 6-mercaptopurine, methotrexate, 5-aminosalicylic acid containing anti-inflammatories (i.e., aminosalicylates), another non-steroidal anti-inflammatory compound, a steroidal anti-inflammatory compound, or antibiotics commonly administered for control of IBD (e.g. ciprofloxacin, metronidazole), or another biologic agent (e.g. TNF alpha antagonists) can be administered in conjunction with a formulation of the present invention.

In an embodiment, the dose of the co-administered medication can be decreased over time during the period of treatment by the liquid pharmaceutical formulation comprising the anti-alpha4beta7 antibody. For example, a patient being treated with a steroid (e.g. prednisone, prednisolone) at the beginning, or prior to, treating with the anti-alpha4beta7 antibody formulation would undergo a regimen of decreasing doses of steroid beginning as early as 6 weeks of treatment with the anti-alpha4beta7 antibody formulation. The steroid dose will be reduced by about 25% within 4-8 weeks of initiating tapering, by 50% at about 8-12 weeks and 75% at about 12-16 weeks of tapering during treatment with the anti-alpha4beta7 antibody formulation. In one aspect, by about 16-24 weeks of treatment with the anti-alpha4beta7 antibody formulation, the steroid dose can be eliminated. In another example, a patient being treated with an anti-inflammatory compound, such as 6-mercaptopurine at the beginning, or prior to, treating with the anti-alpha4beta7 antibody formulation would undergo a regimen of decreasing doses of anti-inflammatory compound similar to the tapering regimen for steroid dosing as noted above.

In one embodiment, the method comprises subcutaneously administering or intramuscularly administering an effective amount of a liquid pharmaceutical formulation of the invention to a patient. In another embodiment, the liquid pharmaceutical formulation can be prepared for self-administration.

The invention also relates to a method for treating a disease associated with leukocyte infiltration of tissues expressing the molecule MAdCAM (e.g., MAdCAM-1). The method comprises administering to a patient in need thereof an effective amount of an anti-alpha4beta7 antibody in a liquid pharmaceutical formulation of the invention. In an embodiment, the disease is graft versus host disease. In some embodiments, the disease is a disease associated with leukocyte infiltration of tissues as a result of binding of leukocytes expressing alpha4beta7integrin to gut-associated endothelium expressing the molecule MAdCAM (e.g., MAdCAM-1). In other embodiments, the disease is gastritis (e.g., eosinophilic gastritis or autoimmune gastritis), pancreatitis, or insulin-dependent diabetes mellitus. In yet other embodiments, the disease is cholecystitis, cholangitis, or pericholangitis.

The invention also relates to a method for treating inflammatory bowel disease in a patient. In one embodiment, the method comprises subcutaneously administering to the patient an effective amount of an anti-alpha4beta7 antibody in a liquid pharmaceutical formulation of the invention. In some embodiments, the inflammatory bowel disease is ulcerative colitis or Crohn's disease. In other embodiments, the inflammatory bowel disease is Celiac disease, enteropathy associated with seronegative arthropathies, microscopic or collagenous colitis, gastroenteritis (e.g., eosinophilic gastroenteritis), or pouchitis.

In some embodiments, treatment with an anti-alpha4beta7 antibody does not alter the ratio of CD4:CD8 lymphocytes. CD4:CD8 ratios can be measured in blood, lymph node aspirate, and cerebro-spinal fluid (CSF). The CSF CD4+: CD8+ lymphocyte ratios in healthy individuals are typically greater than or equal to about 1. (Svenningsson et al., J. Neuroimmunol. 1995; 63:39-46; Svenningsson et al., Ann Neurol. 1993; 34:155-161). An immunomodulator can alter the CD4:CD8 ratio to less than 1.

The invention will be more fully understood by reference to the following examples. They should not, however, be construed as limiting the scope of the invention. All literature and patent citations are incorporated herein by reference.

Example: Impact of Temperature and Concentration
on Antibody Formulation Viscosity An experiment was performed testing various concentrations of anti-alpha4beta7 antibody MLN0002 (vedolizumab) in a liquid formulation to determine the impact of temperature on the viscosity of the various formulations. The results are provided in FIG. 1 and indicate that liquid formulations having an antibody concentration of 140 mg/ml or more (range from 140 mg/ml (circle) to 184 mg/ml (top plus sign)) had a higher viscosity about 35 cP or more at about 3 degrees Celsius versus the same formulations at 25 degrees Celsius, where the viscosity was about 20 cP or less. The higher the antibody concentration, the greater the viscosity measurement, although the difference was especially evident at temperatures less than about 20 degrees Celsius.

SEQUENCE TABLE

| SEQ ID NO: | DESCRIPTION | AMINO ACID SEQUENCE |
|---|---|---|
| 1 | Heavy chain (HC) variable region (amino acid) | QVQLVQSGAEVKKPGASVKVSCKGSGYTFT SYWMHWVRQAPGQRLEWIGEIDPSESNTNY NQKFKGRVTLTVDISASTAYMELSSLRSED TAVYYCARGGYDGWDYAIDYWGQGTLVTVS S |

SEQUENCE TABLE

| SEQ ID NO: | DESCRIPTION | AMINO ACID SEQUENCE |
|---|---|---|
| 2 | HC CDR1 (amino acid) | SYWMH |
| 3 | HC CDR2 (amino acid) | EIDPSESNTNYNQKFKG |
| 4 | HC CDR3 (amino acid) | GGYDGWDYAIDY |
| 5 | Light chain (LC) variable region (amino acid) | DVVMTQSPLSLPVTPGEPASISCRSSQSLA KSYGNTYLSWYLQKPGQSPQLLIYGISNRF SGVPDRFSGSGSGTDFTLKISRVEAEDVGV YYCLQGTHQPYTFGQGTKVEIK |
| 6 | LC CDR1 (amino acid) | RSSQSLAKSYGNTYLS |
| 7 | LC CDR2 (amino acid) | GISNRFS |
| 8 | LC CDR3 (amino acid) | LQGTHQPYT |

What is claimed:

1. An autoinjector comprising a glass syringe comprising a liquid pharmaceutical formulation comprising a humanized anti-alpha4beta7 antibody at a concentration of about 100 mg/mL to 180 mg/mL, a buffer, and an excipient in an amount suitable for achieving a viscosity of the formulation of about 25 cP or less at about 25 degrees Celsius, wherein the formulation has a viscosity of about 35 cP or more at 3 degrees Celsius, wherein the formulation has a pH of about 5 to about 7.5, wherein the antibody is vedolizumab, and wherein the buffer is not citrate, a piston covered in a film to increase lubricity of the piston or a piston formed with a lubricity compound therein, wherein the lubricity of the piston reduces breakloose and glide forces associated with the piston, and a tubular housing comprising a protrusion configured to receive a recess of an activation means and a resilient member disposed at a proximal end of the tubular housing and in engagement with the activation means, wherein the resilient member is a tension spring or a coil spring configured to apply a force on a plunger rod between about 2-20 N, wherein the autoinjector is suitable for subcutaneous self-administration by a human subject.

2. The autoinjector of claim 1, comprising the antibody at a concentration of between about 155 mg/ml and 180 mg/ml.

3. The autoinjector of claim 1, wherein the force applied on the plunger rod is between about 7-13 N.

4. The autoinjector of claim 1, wherein the force applied on the plunger rod is between about 2-9 N.

5. The autoinjector of claim 1, wherein the recess is configured to lock the activation means inside of the tubular housing after injection with the autoinjector.

6. The autoinjector of claim 1, comprising a guiding means configured to cooperate with an interior of the tubular housing to prevent the activation means from rotating in relation to the tubular housing and to move the activation means axially relative to the tubular housing.

7. The autoinjector of claim 1, wherein the formulation has a viscosity of about 20 cP or less at 25 degrees Celsius.

8. The autoinjector of claim 1, comprising a shield system configured to cover a syringe needle of the autoinjector following release of a syringe plunger.

9. The autoinjector of claim 8, wherein the syringe needle comprises three bevels at the tip.

10. The autoinjector of claim 1, wherein the excipient is a sugar.

11. The autoinjector of claim 10, wherein the sugar is sucrose or trehalose.

12. The autoinjector of claim 1, wherein the resilient member is configured to apply a force on a plunger rod of about 10 N.

* * * * *